United States Patent
Labrie et al.

(10) Patent No.: US 6,710,059 B1
(45) Date of Patent: Mar. 23, 2004

(54) METHODS OF TREATING AND/OR SUPPRESSING WEIGHT GAIN

(75) Inventors: Fernand Labrie, Quebec (CA); Yves Deshaies, Quebec (CA); Denis Richard, Quebec (CA); Celine Martel, Quebec (CA); Andre Marette, Quebec (CA)

(73) Assignee: Endorecherche, Inc. (CA)

( * ) Notice: Subject to any disclaimer, the term of this patent is extended or adjusted under 35 U.S.C. 154(b) by 191 days.

(21) Appl. No.: 09/610,286

(22) Filed: Jul. 6, 2000

Related U.S. Application Data

(60) Provisional application No. 60/142,407, filed on Jul. 6, 1999.

(51) Int. Cl.[7] .................... A61K 31/445; C07D 401/00
(52) U.S. Cl. ...................................... 514/320; 546/196
(58) Field of Search ........................ 546/196; 514/320

(56) References Cited

U.S. PATENT DOCUMENTS

| | | | | |
|---|---|---|---|---|
| 5,254,568 A | * | 10/1993 | Kapil et al. | 514/320 |
| 5,446,061 A | * | 8/1995 | Bryant et al. | 514/456 |
| 5,972,888 A | * | 10/1999 | Bue-Valleskey et al. | 514/12 |

FOREIGN PATENT DOCUMENTS

| | | |
|---|---|---|
| EP | 0635264 | 1/1995 |
| EP | 0652006 | 5/1995 |
| EP | 0781555 | 7/1997 |
| WO | WO9310741 | 6/1993 |
| WO | WO9602243 | 2/1996 |
| WO | WO9626201 | 8/1996 |
| WO | WO9902152 | 1/1999 |
| WO | 99/02512 | * 1/1999 |
| WO | WO9917712 | 4/1999 |
| WO | WO9959581 | 11/1999 |
| WO | WO9963974 | 12/1999 |

OTHER PUBLICATIONS

CA 125:1074, abstract of Grese, Bioorg Med Chem Lett, 199, 6(7), pp903–908.*
Ca 122:322542,abstract of Bryant, EP 652006, May 1995.*
S. Luo et al., "Combined Effects of Dehydroepiandrosterone and EM–800 on Bone Mass, Serum Lipids and the Development of Dimethylbenz (A) Anthracene–Induced Mammary Carcinoma in the Rat," Endocrinology 138(10):4435–4444 (1997).
S. Luo et al., "Effects of Combination of Dehydroepian–Drosterone and EM–800 on Bone Mass, Serum Lipids and the Development of Dimethylbenz(A) Antracene (DMBA)–Induced Mammary Carcinoma in the Rat," Breast Cancer Research and Treatment, U.S., NIJHOFF, Boston, Abstracts—Poster Session II 46(1) (Oct. 1997).
S. Couillard et al., "Effect of Dehydroepi–androsterone and the Antiestrogen EM–800 on Growth of Human ZR–75–1 Breast Cancer Xenograft," J. National Cancer Inst. 90(10):772–778 (1998).
S. Luo et al., "Prevention of Development of Dimethylben–z(a)anthracene (DMBA)–Induced Mammary Tumors in the Rat by the New Nonsteroidal Antiestrogen EM–800 (SCH57050)," Breast Cancer Research and Treatment 49(1):1–11 (1998).
F. Labrie et al., "EM–652 (SCH 57068), a Third Generation SERM Acting as Pure Antiestrogen in the Mammary Gland and Endometrium," J. Steroid Biochem. and Mol. Biol. 69:51–84 (1999).
F. Picard et al., "Effects of the Estrogen Antagonist EM–652.HCl on Energy Balance and Lipid Metabolism in Ovariectomized Rats," Int'l. J. Obesity 24:830–840 (2000).
K. Abrahamsson et al., "Transient reduction of human left ventricular mass in carnitine depletion induced by antibiotics containing pivalic acid," Br. Heart J. 74:656–659, 1995.
K. Abrahamsson et al., "Pivalic acid–induced carnitine deficiency and physical excercise in humans," Metabolism 45(12):1501–1507, 1996.
K. Abrahamsson et al., "Effect of short–term treatment with pivalic acid containing antibiotics on serum carnitine concentration—a risk irrespective of age, biochemical and molecular medicine," 55(1):77–79, 1995.
I. Ito et al., "Alteration of ammonia and carnitine levels in short–term treatment with pivalic acid–containing prodrug," Tohoku J. of Exp. Med. 175(1):43–53, 1995.
K. Abrahamsson et al., "Impaired ketogenesis in carnitine depletion caused by short–term administration of pivalic acid prodrug," Biochem. Med. and Met. Biol. 52(1):18–21, 1994.
Y. Toyonaga et al., "Effect of cefditoren povoxil on carnitine metabolism in pediatric patients," Japan Journal of Antibiotics 46(10):926–937, 1993.
M. Tanimura et al., "Carnitine status and safety after administration of S–1108, a new oral cephem, to patients," Antimicrobial Agents and Chemotherapy 37(5):1043–1049, 1993.

* cited by examiner

*Primary Examiner*—D. Margaret Seaman
(74) *Attorney, Agent, or Firm*—Ostrolenk, Faber, Gerb & Soffen LLP

(57) ABSTRACT

Novel methods for the medical treatment and/or prevention of obesity, abdominal fat, and insulin resistance in susceptible warm-blooded animals including humans involves the administration of selective estrogen receptor modulators (SERMs). A combination of a SERM with an amount of estrogen or a sex steroid precursor selected from the group consisting of dehydroepiandrosterone, dehydroepiandrosterone sulfate, androst-5-ene-3b,17b-diol and compounds converted in vivo to one of the foregoing precursors or estrogen is also disclosed.

33 Claims, 8 Drawing Sheets

METHODS OF TREATING AND/OR SUPPRESSING WEIGHT GAIN

This application claims priority of U.S. provisional application No. 60/142,407, filed Jul. 6, 1999.

FIELD OF THE INVENTION

The present invention relates to a method for treating and/or preventing obesity (especially abdominal obesity), and to treating or suppressing the acquisition of abnormal insulin resistance, in susceptible warm-blooded animals including humans. The methods involve administering compounds of the general formula I below, or their pharmaceutical compositions. In other embodiments, the methods involve administering a selective estrogen receptor modulator.("SERM") in combination with a sex steroid precursor.

BACKGROUND OF THE RELATED ART

Obesity, a condition characterized by excessive bodily fat, is a well known risk factor for many diseases such as cardiovascular diseases, hypertension, diabetes and breast cancer. Moreover, personal appearance plays an important part in the overall well-being of most people.

Common treatments of obesity such as various diets (including food restriction diets), weight loss programs and exercise give varying degrees of success for many people. However, there remains a need for other techniques for those who experience insufficient results with prior art techniques, or for use as a supplement to prior art techniques.

Recently, some estrogen agonists/antagonists were disclosed for the treatment or prevention of obesity: Raloxifene and related compounds in European Patent Application Number EP 0 659 423 A1; estrogen agonists having a benzothiophene nucleus in European Patent Application Number EP 0 716 855 A2 ; 3,4-diphenyl chromans in International Application Number PCT/DK96/00011; naphtyl estrogen agonist/antagonist in International Application Number PCT/IB95/00286.

It was also reported that Tamoxifen, another estrogen agonist/antagonist, prevents sulpiride-induced weight gain in female rats (Baptista et al., Pharmacol., Biochem. Behav. (1997), 57(1/2), 215–222). It is also reported that Tamoxifen mimics the effect of estradiol on food intake, body weight and body composition in rats (Wade et al., American Journal of Physiology 1993, 33(6), R1219–1223.)

DHEA has also beneficial effects in the treatment and/or prevention of obesity. In aged Sprague-Dawley rats, Schwartz (in Kent, Geriatrics 37: 157–160, 1982) has observed that body weight was reduced from 600 to 550 g by DHEA without affecting food intake. Schwartz (Cancer 39: 1129–1132, 1979) observed that C3H mice given DHEA (450 mg/kg, 3 times a week) gained significantly less weight and grew older than the control animals, had less body fat and were more active. The reduction in body weight was achieved without loss of appetite or food restriction. Furthermore, DHEA could prevent weight gain in animals bred to become obese in adulthood (in Kent, Geriatrics 37: 157–160, 1982).

DHEA administration to lean Zucher rats decreased body weight gain despite increased food intake. Treated animals had smaller fat pads thus, overall, suggesting that DHEA increases food metabolism, resulting in lower weight gain and fat accumulation (Svec et al., Proc. 2nd Int. Conf. Cortisol and Anti-Cortisols, Las Vegas, Nev., USA, p. 56 abst., 1997).

Obesity was found to be improved in the Avy mutant mouse (Yen et al., Lipids 12: 409–413, 1977) and in the Zucker rat (Cleary and Zisk, Fed. Proc. 42: 536, 1983). DHEA-treated C3H mice had a younger appearance than controls (Schwartz, Cancer Res. 39: 1129–1132, 1979).

Abdominal fat has been associated with metabolic risk factors for coronary breast disease (Imbault et al. Metabolism 1999, 48 (3), 355–62; Ledoux et al. (CMAJ 1997, 157 Suppl.1; 46–53).

SUMMARY OF THE INVENTION

It is accordingly an object of the present invention to reduce adipose tissue, especially abdominal fat.

It is another object of the present invention to reduce risk of coronary heart disease, and other diseases or conditions for which obesity or excess adipose tissues are risk factors.

In one embodiment, the present invention is to provide a novel method for treating or suppressing weight gain in susceptible warm-blooded animals, including humans, said method comprising administering to a subject, in need of such treatment or suppression, a therapeutically effective amount, with or without a pharmaceutical diluent excipient or carrier, of at least one compound of the general formula I:

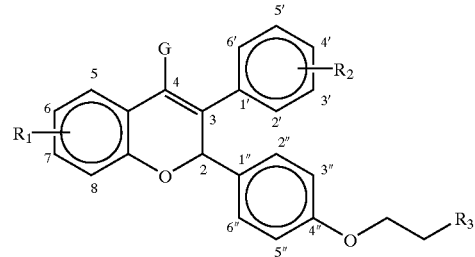

Formula I wherein R1 and R2 are independently selected from the group consisting of hydrogen, hydroxyl, —OM (M being selected from the group consisting of straight or branched C1–C4 alkyl, straight or branched C3–C4 alkenyl, straight or branched C3–C4 alkynyl) and a moiety convertible in vivo to hydroxyl;

wherein G is —H or —CH3; and wherein R3 is a species selected from the group consisting of pyrrolidinyl, piperidino, morpholino, and NRaRb (Ra and Rb being independently hydrogen, straight or branched C1–C6 alkyl, straight or branched C3–C6 alkenyl, and straight or branched C3–C6 alkynyl).

In another embodiment, selective estrogen receptor modulator or pharmaceutically acceptable salt thereof is administered for reducing abdominal fat or reducing the accumulation of abdominal fat.

In another embodiment, sex steroid precursor (e.g. dehydroepiandrosterone, dehydroepiandrosterone sulfate, androst-5-ene-3b,17b-diol) is administered in addition to a Selective Estrogen Receptor Modulator (SERM) for the treatment of obesity or for suppressing weight gain. Human at or over fifty years of age are believed to respond well to the combination therapy, probably because precursor levels tend to undesirably decrease with age.

Thus, in that aspect, the invention provides a method for the treatment of obesity or suppression of weight gain comprising administering to a subject, in need of such suppression or treatment, a therapeutically effective amount with or without a pharmaceutical diluent or carrier, of at least one SERM and an effective amount of a at least one sex steroid precursor selected from the group consisting of dehydroepiandrosterone, dehydroepiandrosterone sulfate, androst-5-ene-3b,17b-diol and compounds converted in vivo to any of the foregoing precursors.

In another aspect, the invention provides a method for treating or reducing the risk of developing insulin resistance comprising administering, to a subject in need of such treatment or reduction, a therapeutically effective amount of at least one SERM. In some embodiments, an effective amount of at least one sex steroid precursor selected from the group consisting of dehydroepiandrosterone, dehydroepiandrosterone sulfate, androst-5-ene-3b,17b-diol and compounds converted in vivo to either is administered also as part of a combination therapy.

In another aspect, the invention provides a kit for the treatment of obesity having a first container which includes at least one SERM and a second container which includes at least one sex steroid precursor selected from the group consisting of dehydroepiandrosterone, dehydroepiandrosterone sulfate, androst-5-ene-3b,17b-diol and compounds converted in vivo to either.

A pharmaceutical excipient carrier or diluent may also be provided in one or more of the containers and may include preservatives and other additives known in the art. The foregoing may also be included with any active ingredient used in any embodiment of the various inventions described herein.

As used herein, a selective estrogen receptor modulator (SERM) is a compound that either directly or through its active metabolite functions as an estrogen receptor antagonist ("antiestrogen") in breast tissue, yet provides estrogen-like effect on body fat, on bone tissue and on serum cholesterol levels (i.e. by reducing serum cholesterol). Non-steroidal compounds that function as estrogen receptor antagonists in vitro or in human or rat breast tissue (especially if the compound acts as an antiestrogen on human breast cancer cells) is likely to function as a SERM. Non-steroidal antiestrogens we have tested and found to function as SERMs include EM-800, EM-652, EM-652.HCl (EM-01538) Raloxifene, Tamnoxifen, Idoxifene, Torimefene, LY 353381, LY 335563, GW 5638 and Droloxifene (described in more detail below). SERMs, in accordance with any embodiment of the invention, are preferably administered at the same dosage as known in the art when these compounds are used as antiestrogens.

Without intending to be bound by theory, it is believed that SERMs, many of which preferably have two aromatic rings linked by one to two carbon atoms, are expected to interact with the estrogen receptor by virtue of the foregoing portion of the molecule that is best recognized by the receptor. Such SERMs also have side chains which may selectively cause antagonistic properties in breast and endometrial tissues without having significant antagonistic properties in other tissues especially bone. Thus, the SERMs may desirably function as antiestrogens in the breast and endometrium while surprisingly and desirably having estrogen-like activity on body fat.

The invention also includes desirably suppressing additional weight gain or desirably providing weight reduction, even if normal weight is not achieved.

As used herein, the term obesity implies an excess of adipose tissue which leads to a weight gain. Prevention and treatment methods of the invention include the inhibition of weight gain and induction of weight loss. The invention includes the treatment of obese humans by reducing their weight to (and maintain the weight at) the normal. The invention also includes the prevention of obesity for persons who are susceptible to acquiring such disease. Patients in need of the invention herein, include those who are overweight (as compared to medically recognized norms) or at risk of becoming overweight.

SERM may also be used to lower blood triglyceride levels in accordance with the invention. For example, EM-800 (described herein) is believed effective for this purpose.

In another embodiment, novel compounds and pharmaceutical compositions for carrying out the invention are provided.

A patient in need of such treatment or reducing the risk of onset of a given disease or condition is one who has either been diagnosed with such disease or one who is susceptible to acquiring such disease. The invention is especially useful for individuals who, due to heredity, environmental factors or other recognized risk factor, are at higher risk than the general population of acquiring the conditions to which the present invention relates.

Except where otherwise stated, the preferred dosage of the active compounds of the invention is identical for both therapeutic and prophylactic purposes. The dosage for each active component discussed herein is the same regardless of the disease being treated (or prevented).

Where two are more different active agents are discussed as part of a combination therapy herein (e.g. an enzyme inhibitor and an antiandrogen), a plurality of different compounds are administered rather than a single compound having multiple activities.

Except where otherwise indicated, the term "compound" and any associated molecular structure may include any possible stereoisomers thereof, in the form of a racemic mixture or in optically active form.

Except where otherwise noted or where apparent from context, dosages herein refer to weight of active compounds unaffected by pharmaceutical excipients, diluents, carriers or other ingredients, although such additional ingredients are desirably included, as shown in the examples herein. Any dosage form (capsule, tablet, injection or the like) commonly used in the pharmaceutical industry is appropriate for use herein, and the terms "excipient", "diluent" or "carrier" include such non-active ingredients as are typically included, together with active ingredients in such dosage forms in the industry. For example, typical capsules, pills, enteric coatings, solid or liquid diluents or excipients, flavorats, preservatives, or the like are included.

In some embodiments, prodrugs of the active ingredients discussed herein (i.e. compounds which convert in vivo to the active ingredients) are used. Many functional groups are known in the pharmaceutical industry to convert in vivo to functional groups of the active compounds discussed herein. See, e.g., Chapter 5 "Design and Application of Prodrugs", A Textbook of Drug Design & Development, Bundgaard & Larsen, Ed., Harwood Academic Publishers GmbH (Chur, Switzerland, 1991). Prodrugs frequently can provide better bioavailability, shelf stability and/or ease of manufacture, corresponding active compounds.

All of the active ingredients used in any of the therapies discussed herein may be formulated in pharmaceutical compositions which also include one or more of the other active ingredients. Alternatively, they may each be administered separately but sufficiently simultaneous in time so that a patient eventually has elevated blood levels or otherwise enjoys the benefits of each of the active ingredients (or strategies) simultaneously. In some preferred embodiments of the invention, for example, one or more active ingredients are to be formulated in a single pharmaceutical composition. In order embodiments of the invention, a kit is provided which includes at least two separate containers wherein the contents of at least two separate containers wherein the contents of at least one container differs, in whole or in part, from the contents of at least one other container with respect to active ingredients contained therein. Two or more different containers are used in the combination therapies of the invention. Combination therapies discussed herein also include use of one active ingredient of the combination in the manufacture of a medicament for the treatment (or prevention) of the disease in question where the treatment or prevention further includes another active ingredient or strategy of the combination.

Abdominal fat is believed different from, and can occur in the absence of, overall bodily obesity. It is also believed to be more of a risk factor in heart disease. Abdominal fat responds favorably to the present invention.

Preferred SERMs of the invention, e.g., those of Formula 1 above, lack undesirable estrogenic effects in the endometrium, a very important improvement relative to SERM therapies utilized in some prior art methods.

SERMs used in the invention are believed to beneficially reduce blood triglycerides and also insulin resistance.

In preferred embodiments discussed herein, the action of SERM is augmented by DHEA or similar sex steroid precursor.

Without intending to be bound by theory, one explanation of the synergy obtained by combining SERMs and precursors could be at least partial differences in their mechanisms of action. DHEA, for example, appears to increase food metabolism without suppressing appetite. EM-652.HCl, a SERM, appears to suppress food intake.

BRIEF DESCRIPTION OF THE DRAWINGS

FIG. 8. Shows the effect of a 20-day treatment on Soleus weight (data expressed in grams (g) as the means±SEM) and lipoprotein lipase (data expressed in ?U/g protein as the means±SEM; *p<0.05 vs intact group); in intact rats, ovariectomized rats and ovariectomized rats treated with estradiol and EM-652.HCl.

DETAIL DESCRIPTION OF THE INVENTION

Figure 1:
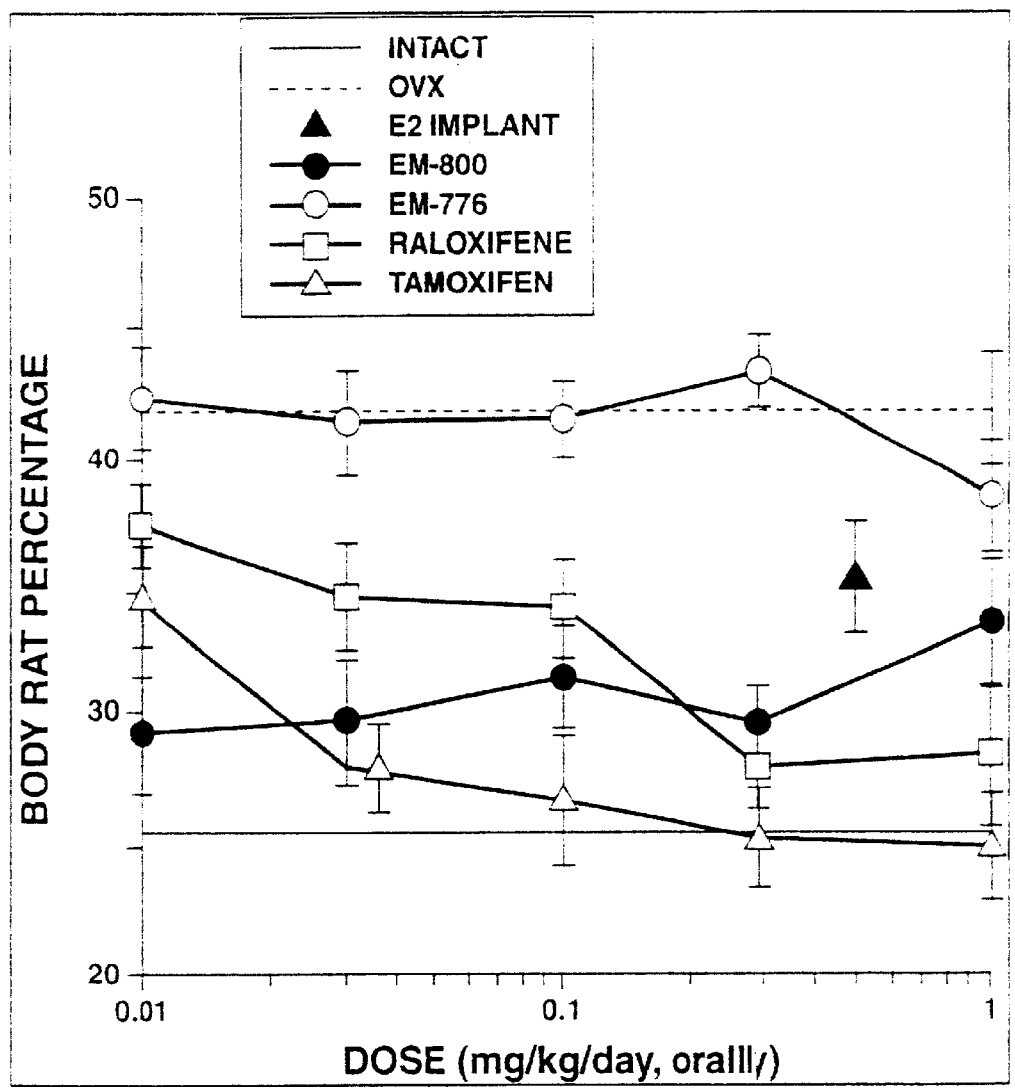
FIG. 1. Shows the effect of 35-week treatment with increasing doses (0.01, 0.03, 0.1, 0.3, 1 mg/kg, orally, once daily) of SERMs EM-800, raloxifene, tamoxifen, and an inactive enantiomer, EM-776 (eniantomer of EM-800) on total body fat in ovariectomized rat. Data are expressed as the means±SEM. **:P<0.01 experimental versus respective control.

It is preferred to administer a pharmaceutical composition comprising a pharmaceutically acceptable excipient, diluent or carrier and a therapeutically effective amount of a selective estrogen receptor modulator having the following general formula I:

wherein R1 and R2 are independently selected from the group consisting of hydrogen, hydroxyl, —OM (M being selected from the group consisting of straight or branched C1–C4 alkyl, straight or branched C3–C4 alkenyl, straight or branched C3–C4 alkynyl) and a moiety convertible in vivo to hydroxyl;

wherein G is —H or —CH3;wherein R3 is a species selected from the group consisting of pyrrolidinyl, piperidino, morpholino, and NRaRb (Ra and Rb being independently hydrogen, straight or branched C1–C6 alkyl, straight or branched C3–C6 alkenyl, and straight or branched C3–C6 alkynyl, and a sex steroid precursor selected from the group consisting of dehydroepiandrosterone, dehydroepiandrosterone sulfate, androst-5-ene-3b,17b-diol and compounds converted in vivo to either.

A SERM according to the above formula I provides the unexpecxted advantage of having little or no estrogenic effect on the endometrium unlike the SERMs known in the prior art.

It is preferred that the SERM of the invention be optically active and have greater than 50% of a stereoisomer compound having an absolute configuration S on carbon 2.

It is also preferred for reasons of stability and water solubility (bioavailability) that the SERM of the invention is a salt of a compound of the formula I and of an acid selected from the group consisting of acetic acid, adipic acid, benzenesulfonic acid, benzoic acid, camphorsulfonic acid, citric acid, fumaric acid, hydroiodic acid, hydrobromic acid, hydrochloric acid, hydrochlorothiazide acid, hydroxynaphthoic acid, lactic acid, maleic acid, methanesulfonic acid, methylsulfuric acid, 1,5-naphthalenedisulfonic acid, nitric acid, palmitic acid, pivalic acid, phosphoric acid, propionic acid, succinic acid, sulfuric acid, tartaric acid, terephthalic acid, p-toluenesulfonic acid, and valeric acid.

One preferred compound of the invention is EM-800 reported in PCT/CA96/00097 (WO 96/26201) The molecular structure of EM-800 is:

Another more preferred compound of the invention is EM-652.HCl (also called EM-01538):

EM-652.HCl provides additional advantages over other SERMs such as EM-800 because it does not contain pivaloyl groups that can enhance the risk of a decrease in serum carnitine levels.

Other preferred SERMs of the invention include Tamoxifen((Z)-2-[4-(1,2-diphenyl-1-butenyl)]-N,N-dimethylethanamine) (available from Zeneca, UK), Toremifene (available from Orion-Farmos Pharmaceuticla, Finland, or Schering-Plough), Droloxifene and CP-336,156 (cis-1R-[4'-pyrrolidino-ethoxyphenyl]-2S-phenyl-6-hydroxy-1,2,3,4,-tetrahydronapthalene D-(–)-tartrate salt) (Pfizer Inc., USA described in U.S. Pat. No. 5,889,042) (also called Lasofoxifene) Raloxifene (Eli Lilly and Co., USA), LY 335563 and LY 353381 (Eli Lilly and Co., USA described in WO 98/45287, WO 98/45288, and WO 98/45286), Idoxifene (SmithKline Beecham, USA), Levormeloxifene (3,4-trans-2,2-dimethyl-3-phenyl-4-[4-(2-(2-(pyrrolidin-1-yl)ethoxy)phenyl]-7-methoxychroman) (Novo Nordisk, A/S, Denmark) which is disclosed in Shalmi et al. WO 97/25034, WO 97/25035, WO 97/25037,WO 97/25038; and Korsgaard et al. WO 97/25036), GW5638 (described by Willson at al., Endocrinology, 138(9), 3901–3911, 1997) and indole derivatives (disclosed by Miller et al. EP 0802183A1) and TSE 424, and ERA 923 developed by Wyeth Ayerst (USA) and disclosed in JP10036347 (American home products corporation) and nonsteroidal estrogen derivatives described in WO 97/32837. Other SERMs of the invention are disclosed in: WO 99/07377; WO 98/48806; EP 0823437A2; EP 0838464A1; EP 0835867A1, EP 0835868A1; EP 0792641A1; EP 0873992A1 and EP 0895989A1.

Any SERM used as required for efficacy (as recommended by the manufacturer for the treatment and/or prevention of osteoporosis or breast cancer) can be used. Appropriate dosages are known in the art. Any other non steroidal antiestrogen commercially available can be used according to the invention. Any compound having activity similar to SERMs (example: Raloxifene can be used).

SERMs administered in accordance with the invention are preferably administered in a dosage range between 0.01 to 10 mg/kg of body weight per day (preferably 0.05 to 1.0 mg/kg), with 60 mg per day, especially 20 mg per day, being preferred for a person of average body weight when orally administered, or in a dosage range between 0.003 to 3.0 mg/kg of body weight per day (preferably 0.015 to 0.3 mg/kg body weight), with 20 mg per day, especially 10 mg per day, being preferred for a person of average body weight when parentally administered (i.e. intramuscular, subcutaneous or percutaneous administration). Preferably the SERMs are administered together with a pharmaceutically acceptable diluent or carrier as described below.

Preferred sex steroid precursors are dehydroepiandrosterone (DHEA) (available from Diosynth Inc., Chicago, Ill., USA), its prodrugs (available from Steraloids, Wilton, N.H., USA), 5-androsten-3b,17b-diol and its prodrugs androst-5-ene-3b,17b-diol 3-acetate and androst-5-ene-3b,17b-diol dihemisuccinate (available from Steraloids, Wilton, N.H. USA).

dosages as necessary where a given patients' metabolism or reaction to treatment is atypical.

Treatment in accordance with the invention is suitable for indefinite continuation. It is expected that DHEA and/or 5-diol or other precursor, treatment will simply maintain DHEA levels within a range similar to that which occurs naturally in women before menopause (serum concentration between 4 and 10 micrograms per liter), or naturally in androst-5-ene-3b,17b-diol 3-acetate

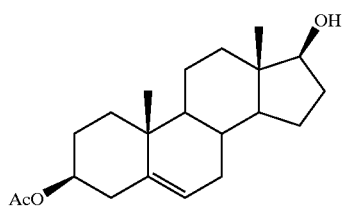

androst-5-ene-3b,17b-diol dihemisuccinate

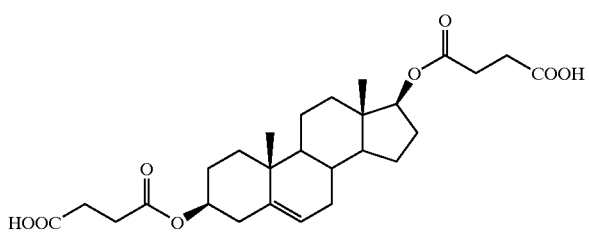

The sex steroid precursor can be formulated as an alcoholic gel containing 2.0 to 10% of caprylic-capric triglyceride (Neobee M-5); 10 to 20% of hexylene glycol; 2.0 to 10% of diethyleneglycol monomethyl ether (Transutol); 2.0 to 10% of Cyclomethicone (Dow Coming 345); 1.0 to 2% of benzyl alcohol and 1.0 to 5.0% of hydroxypropylcellulose (Klucel HF).

The carrier (for either the SERM or precursor) may also include various additives commonly used in the pharmaceutical industry. For example, fragrances, antioxidants, perfumes, gelling agents, thickening agents such as carboxymethylcellulose, surfactants, stabilizers, emollients, coloring agents and other similar agents may be present. When active ingredients are administered transdermally, the site of application on the skin should be changed in order to avoid excess local concentration of active ingredient and possible overstimulation of the skin and sebaceous glands by androgenic metabolites of sex steroid precursor.

In a pharmaceutical composition for oral administration, DHEA or other precursor is preferably present in a concentration between 5 and 98% by weight relative to total weight of the composition more preferably between 50 and 98 percent, especially between 80 and 98 percent. A single precursor such as DHEA may be the only active ingredient, or alternatively, a plurality of precursors and/or their analogues may be used (e.g., a combination of DHEA, DHEA-S, 5-diol, or a combination of two or more compounds converted in vivo to DHEA, DHEA-S or 5-diol or a combination of DHEA or 5-diol and one or more analogues thereof which are converted to DHEA or 5-diol in vivo, etc. The blood level of DHEA is the final criteria of adequate dosage which takes into account individual variation in absorption and metabolism.

Preferably, the attending clinician will, especially at the beginning of treatment, monitor an individual patient's overall response and serum levels of DHEA (in comparison to the preferred serum concentrations discussed above), and monitor the patient's overall response to treatment, adjusting young adult men (serum concentration between 4 and 10 micrograms per liter).

The SERM compound and/or the sex steroid precursor can also be administered, by the oral route, and may be formulated with conventional pharmaceutical excipients, e.g. spray dried lactose, microcrystalline cellulose, and magnesium stearate into tablets or capsules for oral administration.

The active substance can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycol. Of course, taste-improving substances can be added in the case of oral administration forms.

As further forms, one can use plug capsules, e.g. of hard gelatin, as well as closed solf-gelatin capsules comprising a softner or plasticizer, e.g. glycerine. The plug capsules contain the active substance preferably in the form of granulate, e.g. in mixture with fillers, such as lactose, saccharose, mannitol, starches, such as potato starch or amylopectin, cellulose derivatives or highly dispersed silicic acids. In solf-gelatin capsules, the active substance is preferably dissolved or suspended in suitable liquids, such as vegetable oils or liquid polyethylene glycols.

Lotion, ointment, gel or cream forms are possible and should be thoroughly rubbed into the skin so that no excess is plainly visible, and the skin should not be washed in that region until most of the transdermal penetration has occurred preferably at least 4 hours and, more preferably, at least 6 hours.

A transdermal patch may be used to deliver precursor or SERM in accordance with known techniques. It is typically applied for a much longer period, e.g., 1 to 4 days, but typically contacts active ingredient to a smaller surface area, allowing a slow and constant delivery of active ingredient.

A number of transdermal drug delivery systems that have been developed, and are in use, are suitable for delivering the active ingredient of the present invention. The rate of release is typically controlled by a matrix diffusion, or by passage of the active ingredient through a controlling membrane.

A number of transdermal drug delivery systems that have been developed, and are in use, are suitable for delivering the active ingredient of the present invention. The rate of release is typically controlled by a matrix diffusion, or by passage of the active ingredient through a controlling membrane.

Mechanical aspects of transdermal devices are well known in the rat, and are explained, for example, in U.S. Pat. Nos. 5,162,037, 5,154,922, 5,135,480, 4,666,441, 4,624,665, 3,742,951, 3,797,444, 4,568,343, 5,064,654, 5,071,644, 5,071,657, the disclosures of which are incorporated herein by reference. Additional background is provided by European Patent 0279982 and British Patent Application 2185187.

The device may be any of the general types known in the art including adhesive matrix and reservoir-type transdermal delivery devices. The device may include drug-containing matrixes incorporating fibers which absorb the active ingredient and/or carrier. In a reservoir-type device, the reservoir may be defined by a polymer membrane impermeable to the carrier and to the active ingredient.

In a transdermal device, the device itself maintains active ingredient in contact with the desired localized skin surface. In such a device, the viscosity of the carrier for active ingredient is of less concern than with a cream or gel. A solvent system for a transdermal device may include, for example, oleic acid, linear alcohol lactate and dipropylene glycol, or other solvent systems known in the art. The active ingredient may be dissolved or suspended in the carrier.

For attachment to the skin, a transdermal patch may be mounted on a surgical adhesive tape having a hole punched in the middle. The adhesive is preferably covered by a release liner to protect it prior to use. Typical material suitable for release includes polyethylene and polyethylene-coated paper, and preferably silicone-coated for ease of removal. For applying the device, the release liner is simply peeled away and the adhesive attached to the patient's skin. In U.S. Pat. 5,135,480, the disclosure of which is incorporated by reference, Bannon et al. describe an alternative device having a non-adhesive means for securing the device to the skin.

The percutaneous or transmucosal delivery system of the invention may also be used as a novel and improved delivery system for the prevention and/or treatment of obesity.

EXAMPLES OF EFFECTIVENESS OF THE METHODS OF THE INVENTION

Example 1

Effect of 35-week treatment with compounds of the invention on total body fat and body weight of ovariectomized rat.

Materials and Methods

Animals and Treatment

Ten to twelve week-old female Sprague-Dawley rats (Crl:CD(SD)Br) (Charles River Laboratory, St-Constant, Canada) weighing approximately 225–250 g at start of treatment were used. The animals were acclimatized to the environmental conditions (temperature: 22±3° C.; humidity: 50±20%; 12-h light-12-h dark cycles, lights on at 07:15 h) for 1 week before starting the experiment. The animals were housed three per cage and were allowed free access to tap water and a pelleted certified rodent feed (Lab Diet 5002, Ralston Purina, St-Louis, Mo.). The experiment was conducted in a Canadian Council on Animal Care approved facility in accordance with the CCAC Guide for Care and Use of Experimental Animals.

Two hundred seventy-six rats were randomly distributed between 23 groups of 12 animals each as follows: 1) Intact control; 2) OVX control; 3 to 7) OVX+EM-800 (0.01, 0.03, 0.1, 0.3 or 1 mg/kg); 8 to 12) OVX+Raloxifene (0.01, 0.03, 0.1, 0.3 or 1 mg/kg); 13 to 17) OVX+Tamoxifene (0.01, 0.03, 0.1, 0.3 or 1 mg/kg); 18 to 22) OVX+EM-776 (0.01, 0.03, 0.1, 0.3 or 1 mg/kg); 23) OVX+estradiol (E2, implant). On day 1 of the study, the animals of the appropriate groups were bilaterally ovariectomized (OVX) under isoflurane anesthesia. One Silastic implant of estradiol (E2) was inserted subcutaneously in the dorsal area of each animal of group 13. The implants had the following E2 concentration and size: E2 (E2: cholesterol (1:100, w:w)), 0.5 cm (length), 0.125 inch (outer diameter) and 0.062 inch (inner diameter). During the course of the experiment, the E2 implants were replaced monthly. Treatment with EM-800, Raloxifene, Tamoxifene, and EM-776 or vehicle (4% ethanol, 4% polyethylene glycol-600, 1% gelatin and 0.9% NaCl) was initiated on day 2 of the study. The appropriate compound or vehicle alone was given once daily by oral gavage in 0.5 ml/rat for 37 weeks. Approximately 24 hours after the last dosing, overnight fasted animals were killed by exsanguination at the abdominal aorta under isoflurane anesthesia.

Fat Body Composition

After 35 weeks of treatment, individual rats under anesthesia with isoflurane had their whole body skeleton as well as their right femur scanned using dual energy x-ray absorptiometry (DEXA; QDR 4500A, Hologic, Waltham, Mass.) and a Regional High Resolution Scan software. The scan field size used for the whole body was 30.492×17.912 cm, the resolution was 0.1512×0.0640 cm and the scan speed was 2.499 mm/sec. The fat body composition of the whole body was determined.

Statistical Analyses

Data are expressed as the means±SEM. Statistical significance was determined according to the multiple-range test of Duncan-Kramer (1956).

Results

The effect of increasing daily oral doses of EM-800, Raloxifene, Tamoxifene, and EM-776 on body fat as measured in vivo by DEXA is illustrated in FIG. 1. It can be seen that EM-800 at the lowest dose of 0.01 mg/kg decreases by 78% the OVX-induced stimulation of body fat, Raloxifene is less active than EM-800 while EM-776, the enantiomer of EM-800, has no significant effect. In table 1, the effects of EM-800 or Raloxifene on body weight in ovariectomized rats are reported. Comparison is made with intact and ovariectomized control rats. It can be seen also that small doses of EM-800 achieve weight control similar to significantly greater amounts or Raloxifene (e.g. 0.03 mg/kg EM-800 achieves similar results to 0.3 mg/kg Raloxifene). Both substantially reverse ovariectomization induced weight gain at much higher doses.

TABLE 1

| Group | Body Weight at Necropsy g |
| --- | --- |
| Intact control | 356 ± 16** |
| OVX control | 491 ± 16 |
| OVX + EM-800 (0.01 mg/kg) | 385 ± 17** |

TABLE 1-continued

| Group | Body Weight at Necropsy g |
|---|---|
| OVX + EM-800 (0.03 mg/kg) | 364 ± 10** |
| OVX + EM-800 (0.1 mg/kg) | 369 ± 17** |
| OVX + EM-800 (0.3 mg/kg) | 359 ± 7** |
| OVX + EM-800 (1 mg/kg) | 368 ± 6** |
| OVX + Raloxifene (0.01 mg/kg) | 439 ± 13* |
| OVX + Raloxifene (0.03 mg/kg) | 451 ± 14* |
| OVX + Raloxifene (0.1 mg/kg) | 389 ± 14** |
| OVX + Raloxifene (0.3 mg/kg) | 367 ± 9** |
| OVX + Raloxifene (1 mg/kg) | 342 ± 12** |

Example 2

11-month combination treatment with compounds of the invention.

1. Test Materials
   1.1 Test Compounds
   DHEA: Available from Steraloids Inc. Wilton, N.H. Lot: H137;
   EM-800 is synthesized at the UCPO Department of Lab. of Mol. Endo., CHUL.
   1.2 Vehicle
   a) Gelatin: Lab-Grade, ACP Chemicals Inc., Montreal, Qc. Lot# F0195
   b) Ethanol: Commercial Alcohols Inc., Brampton, Ontario. Lot No. 11296
   c) Polyethylene Glycol-600 (PEG-600): Omega Chemical Company Inc., Lévis, Quebec. Lot#: 00–0117-EZ
   d) Normal Saline: 0.9% Sodium Chloride irrigation USP. Abbott Laboratories Limited, St-Laurent, Qc
   e) Propylene Glycol (1,2-Propanediol, PPG): Sigma Chemical Co., St-Louis, Mo.
   g) Vehicle 1: 4% ETOH-4% PEG-600-1% gelatin-0.9% NaCl-H2O for Subcutaneous Injection.
   h) Vehicle 2: 50% ETOH-50% PPG for Topical Application.
2. Test Animal Specifications
   2.1 Species: *Rattus norvegicus*
   2.2 Strain: Sprague-Dawley Rat (Crl:CD® (SD) BR VAF/PlusTM)
   2.3 Sex: Female
   2.4 Source: Charles River Canada Inc., 188 Lasalle Road, St. Constant, Quebec, 1-800-561-4975
   2.5 Age at start of dosing: rats of G18–29 were 16-week-old
   2.6 Housing and maintenance
   a) Housing: The rats were housed 2–3 per cage in shoe boxes. All cages were clearly labeled with a cage label indicating protocol number, group number and animal number.
   b) During the study, environmental conditions in the room will be controlled (targeted conditions: temperature 20 to 25° C.; humidity: 50±20%.). Photoperiod will be 12 hours light: 12 hours dark.
   c) Diet and Water: Rodent Diet (pellets), and tap water will be provided ad libitum.
   2.7 Acclimatation Period: At least two weeks.
   2.8 Randomization: Rats will be randomly assigned to each group at arrival.
   2.9 Method of Euthanasia: Isoflurane-induced general anesthesia.
3. Methods and Experimental Design
   1 INTACT 11 rats/group
   2 OVX CONT total 44 rats
   3 OVX+DHEA 12.5 mg
   4 OVX+DHEA 12.5 mg+EM-800 (100 μg)
   3.1 Preparation of vehicle and test articles
   a) Preparation of EM-800:
   EM-800 or both of them will be dissolved in ETOH:PEG-600 (1:1) with agitation on Fisher Scientific Stirring Hot Plate, then, 1% GNS will be added to the required volume.
   b) Preparation of DHEA:
   DHEA is dissolved in 50% ETOH, 50% PPG by agitation.
   3.2 Animal preparation and treatments:
   Animals will be treated once daily as indicated on Item 6.1. DHEA, prepared in 50% ETOH, 50% PPG, will be percutaneously applied (P.C.) to corresponding animals once daily (I.D.) in a volume of 0.5 ml. EM-800 will be prepared in 4% ETOH, 4% PEG-600, 1% Gelatin, 0.9% NaCl, and will be subcutaneously administered to the animals of corresponding groups once daily (S.C., I.D.) in a volume of 0.5 ml
   The rats are subcutaneously injected with 0.5 ml of vehicle 1 if they are not subcutaneously treated with any test compound, and are topically applied with 0.5 ml of vehicle 2 if they are not treated with 5-DIOL nor DHEA.
   3.3 Observations and measurements
   a) Clinical Observations:
   Each rat will be observed at least once daily for general manifestation.
   b) Body Weights:
   Rats will be weighed at the start and the end of the protocol, and every three months during the treatment.
4. Results As shown in the table 2, the effect of treatment with DHEA at the daily dose of 12.5 mg decreases by 87% the OVX stimulation of body weight. Administration of EM-800 at the daily dose of 100 mg gives a synergistic effect and a 140% inhibition of the OVX stimulation of the body weight is obtained.

TABLE 2

| Treatment | Total Weight (g) |
|---|---|
| Intact | 479.5 ± 20.4 |
| OVX | 567.4 ± 25.7 |
| OVX + DHEA (12.5 mg/day/rat) | 490.8 ± 24.1 |
| OVX + DHEA (12.5 mg/day/rat) + EM-800 (100 μg/day/rat) | 444.5 ± 20.5 |

Example 3

Effect of a 20-day treatment with EM-652.HCl on body fat and body weight parameters in ovariectomized rats.

Materials and Methods

Animals and Treatment

Eight to ten week-old female Sprague-Dawley rats (Crl:CD(SD)Br) (Charles River Laboratory, St-Constant, Canada) weighing approximately 200–225 g at the start of treatment were used. The animals were acclimatized to the environmental conditions (temperature: 22±3° C.; 10-h light-14-h dark cycles, lights on at 06:00h) for 1 week before starting the experiment. The animals were housed individually in stainless steel cages of conventional design and were allowed free access to tap water and a high carbohydrate mixed diet composed of (g/100 g): Corn starch, 31.2; Dextrose, 31.2; Casein, 20.0; corn oil, 6.4; dl-Methionine, 0.3; Vitamine mix, 1.0; AIN-76 mineral mix, 4.9 and fiber, 5.0. The experiment was conducted in a Canadian Council on Animal Care approved facility in accordance with the CCAC Guide for Care and Use of Experimental Animals.

Forty rats were randomly distributed between 4 groups of 10 animals each as follows: 1) Intact control; 2) OVX control; 3) OVX+EM-652.HCl (0.5 mg/rat, ~2.5 mg/kg); 4) OVX+estradiol (E2, implant). On day 1 of the study, the animals of the appropriate groups were bilaterally ovariectomized (OVX) under isoflurane anesthesia. One Silastic implant of estradiol (E2) was inserted subcutaneously in the dorsal area of each animal of group 4. The implants, chosen in preliminary experiments to give physiological levels of E2, had the following steroid concentration and size: E2: cholesterol (1:50, w:w), 0.5 cm (length of diluted steroid in silastic tubing), 0.125 inch (outer diameter of silastic tubing) and 0.062 inch (inner diameter of silastic tubing). Estradiol implants were immersed in 0.9% NaCl at 37° C. overnight before their subcutaneous insertion in animals. The treatment with EM-652.HCl or vehicle alone (0.4% methylcellulose in water) was initiated on day 2 of the study. The compound or vehicle was given once daily by oral gavage in 0.5 ml/rat for 20 days. Body weights and food consumption were recorded every 2 days.

Figure 2:
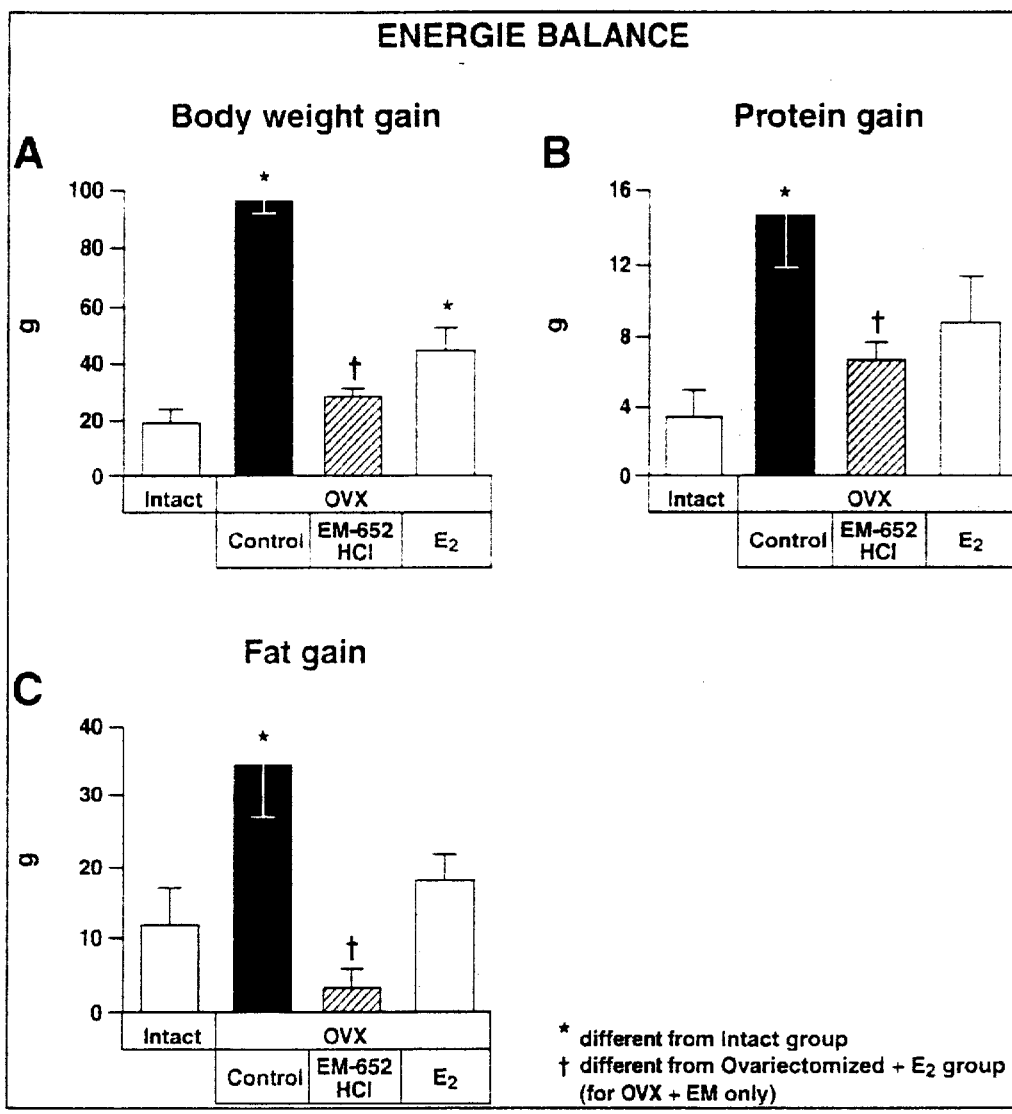
FIG. 2. Shows the effect of a 20-day treatment on body weight gain (A), protein gain (B) and fat gain (C) in intact rats, ovariectomized rats, and ovariectomized rats treated with SERM EM-652.HCl or with estradiol. Data are expressed in grams (g) as the means±SEM. *p<0.05 vs intact group; †p<0.05 vs OVX+E2 group (for EM-652.HCl group only).
Figure 3:
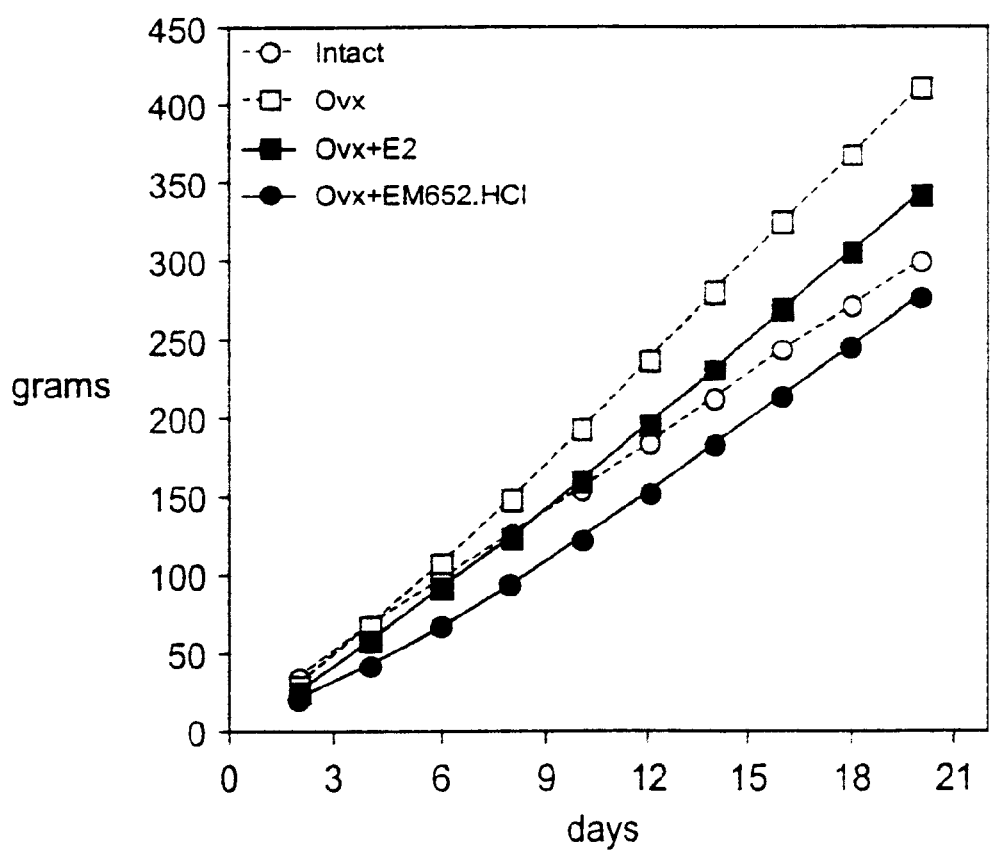
FIG. 3. Shows the effect of a 20-day treatment on cumulative food intake in intact rats, ovariectomized rats, and ovariectomized rats treated with EM-652.HCl or estradiol. Data are expressed in grams (g).

Approximately 24 hours after the last dosing, overnight fasted animals were anesthesized with ketamine-xylazine and blood drawn by cardiac puncture. The blood was collected as well as white and brown adipose tissues.
Body Weight, Food Intake, and Body Gains in Energy, Fat, and Protein Measurements Body weight, food intake, and body gains in energy, fat, and protein were determined according to Deshaies et al, Am. J. Physiol., 1997; 273, E355–E362 (1997).
Tissue Measurements Lipoprotein lipase activities were determined according to Deshaies et al, Am. J. Physiol., 1997; 273, E355–E362 (1997).
Results It can be seen in FIGS. 2A and C that the 20-day treatment with EM-652.HCl completely reversed the 4-fold body weight gain and the 3-fold fat gain, respectively, observed after ovariectomy, while this effect was less accentuated on protein gain (FIG. 2B). Estradiol had a smaller effect. The cumulative food intake is shown in FIG. 3. Treatment effects reflected those on body weight gain. Estradiol partially prevented the increase in food intake due to Ovx, while EM-652.HCl did so more efficiently than estradiol, reducing food intake to a value lower than that of intact animals.

The major variables of energy balance are summarized in table 3. Ovx increased digestible energy intake by 44%. Estradiol reduced energy intake in Ovx animals, but total energy intake remained 17% higher than that of intact animals, while EM-652.HCl completely prevented the Ovx-induced increase in energy intake. Energy gain was proportional to food intake. Again, estradiol reduced energy gain (to levels not significantly different from those of intact rats), but EM-652.HCl was more efficient (significantly different from estradiol).

Food efficiency was increased by Ovx, reduced in Ovx animals by E2, and further reduced by EM-652.HCl.

Figure 4:
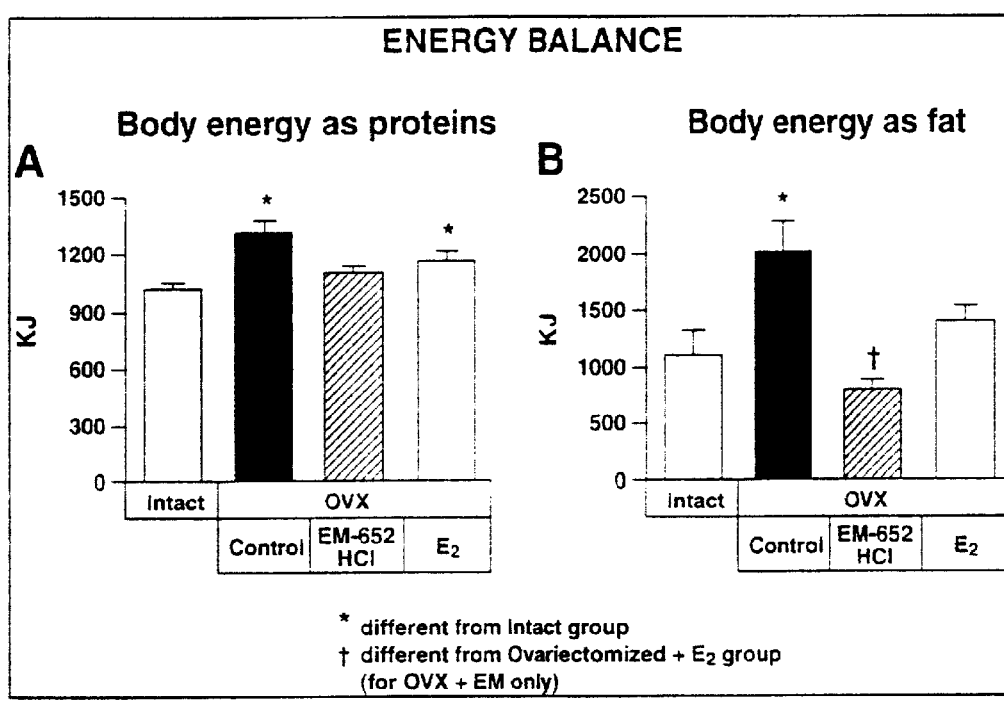
FIG. 4. Shows the effect of a 20-day treatment on body energy as proteins (A) and body energy as fat (B) in intact rats, ovariectomized rats and ovariectomized rats treated with EM-652.HCl or estradiol. Data are expressed in kilojoules (Kj) as the means±SEM; *p<0.05 vs intact group; †p<0.05 vs OVX+E2 group (for EM-652.HCl group only).
Figure 5:
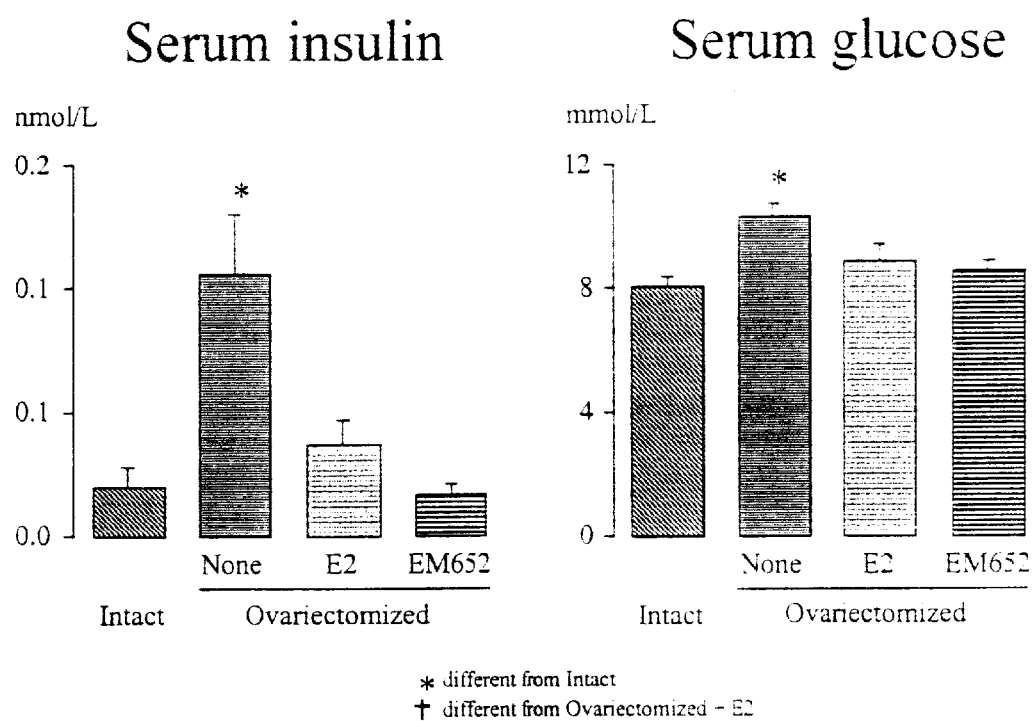
FIG. 5. Shows the effect of a 20-day treatment on serum insulin levels and serum glucose levels in intact rats, ovariectomized rats and ovariectomized rats treated with EM-652.HCl or estradiol. Data are expressed in nmol/L as the means±SEM; *p<0.05 vs intact group.

The 30% increase in body energy from proteins following ovariectomy as well as the 80% increase in body energy from fat were also completely reversed by EM-652.HCl treatment as can be seen in FIGS. 4A and B. As shown in FIG. 5A, the development of insulin resistance in Ovx animals was confirmed by the presence of fasting hyperinsulinemia (which is usually proportional to the degree of insulin resistance) and fasting hyperglycemia (a reflection of the loss of effectiveness of insulin to maintain normal levels of blood glucose). Both estradiol and EM-652.HCl prevented the Ovx-induced insulin resistance.

Figure 6:
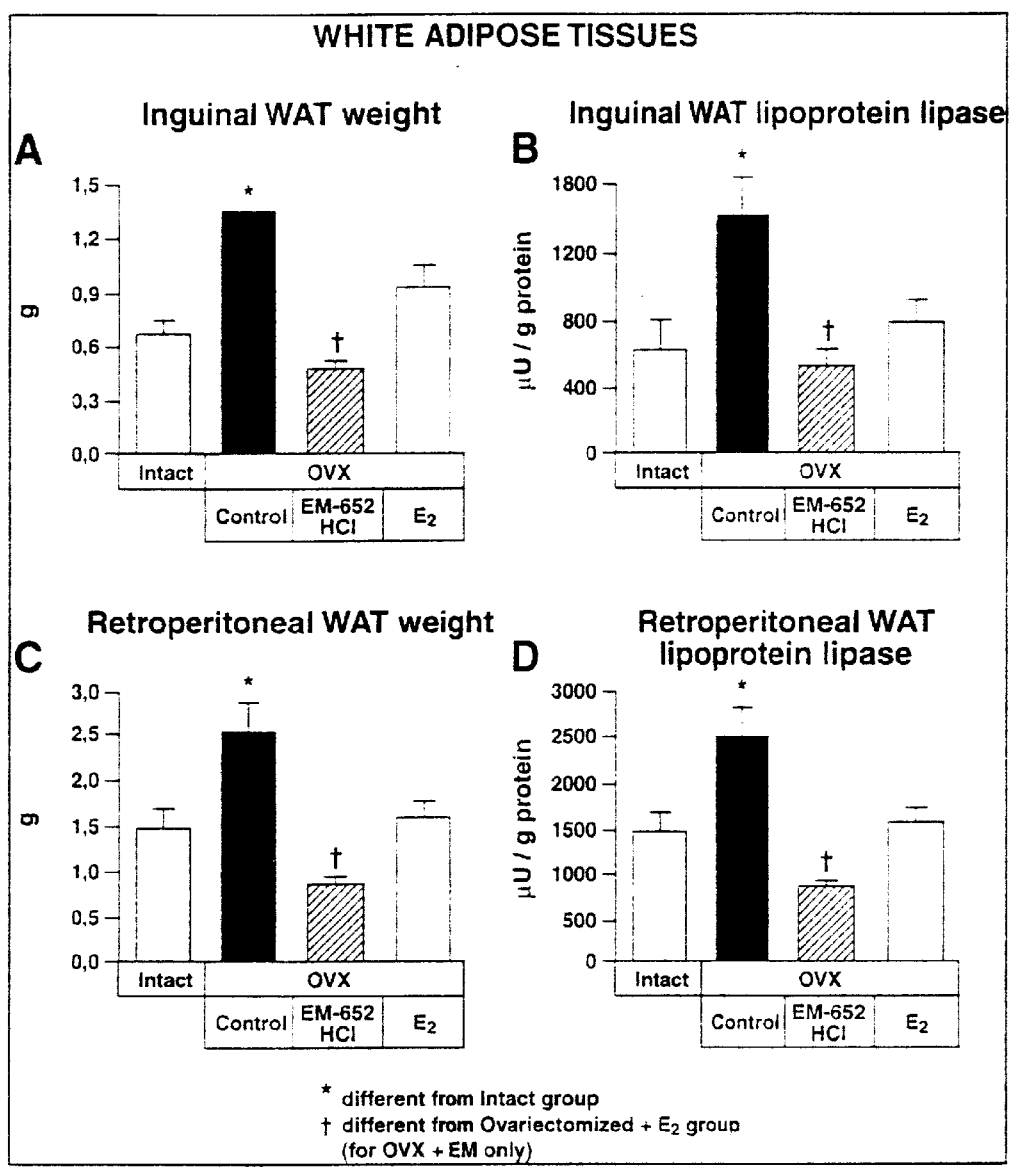
FIG. 6. Shows the effect of a 20-day treatment on white adipose tissue parameters: inguinal (A) and retroperitoneal (C) adipose tissue weight (data expressed in grams (g) as the means±SEM), inguinal (B) and retroperitoneal (D) white adipose tissue lipoprotein lipase activity (data expressed in ?U/g protein as the means±SEM; *p<0.05 vs intact group; †p<0.05 vs OVX+E2 group (for EM-652.HCl group only)), in intact rats, ovariectomized rats and ovariectomized rats treated with EM-652.HCl or estradiol.

FIGS. 6A and 6C show that OVX increased the mass (amounts) of inguinal and retroperitoneal adipose tissues which are representative of the observed change in total body fat. This increase was completely abolished by EM-652.HCl treatment. With estradiol, the effect was less important. The same pattern is shown in FIG. 6B and 6D where lipoprotein lipase activity is reported. This enzyme modulates the intravascular hydrolysis of triglycerides and thereby the entry of fatty acids into adipose stores.

Figure 7:
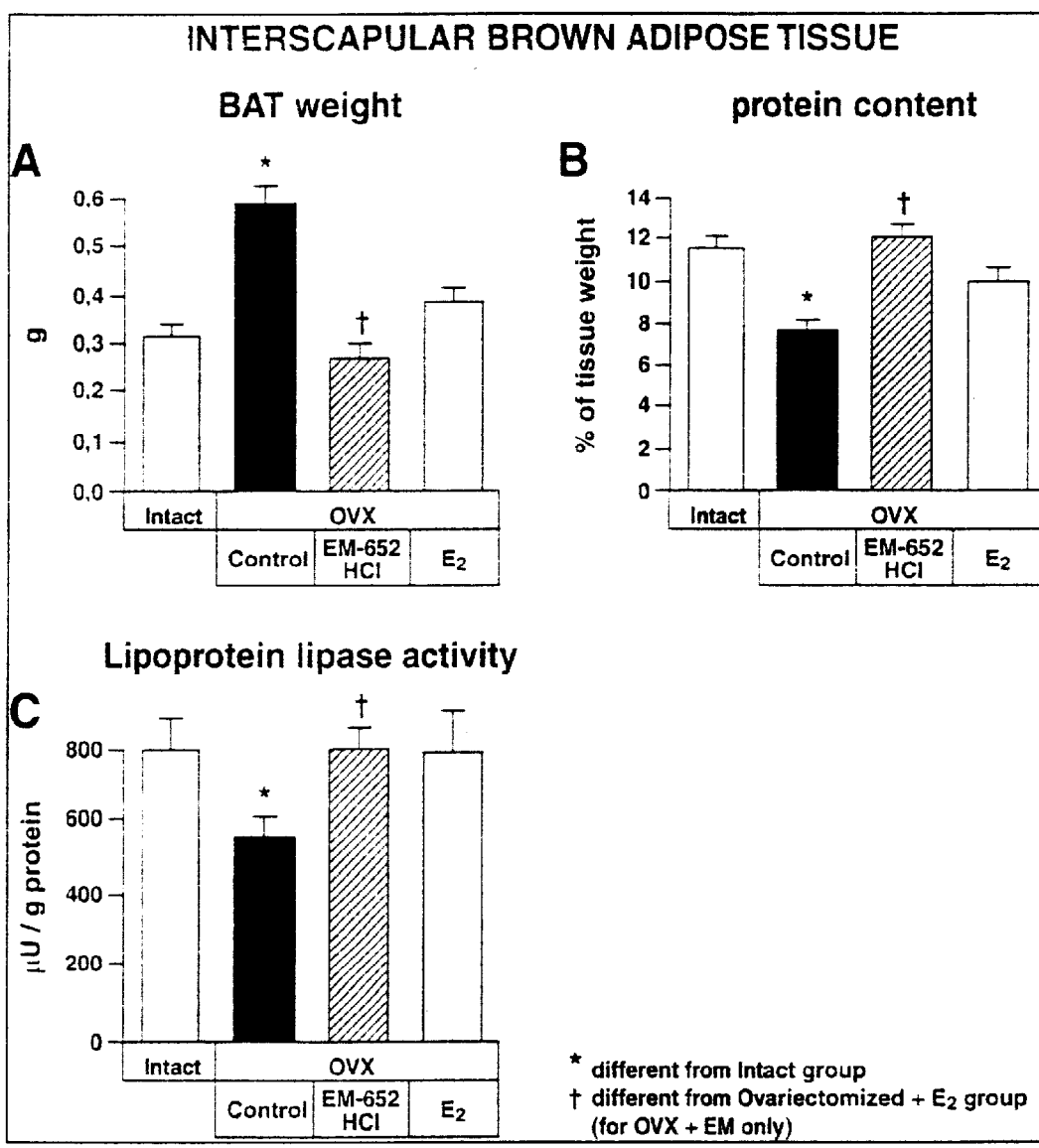
FIG. 7. Shows the effect of a 20-day treatment on interscapular brown adipose tissue parameters: (A) brown adipose tissue weight (data expressed in grams (g) as the means±SEM, *p<0.05 vs intact group; †p<0.05 vs OVX+E2 group (for EM-652.HCl group only)); (B) protein content (data expressed in % of tissue weight as the means±SEM; *p<0.05 vs intact group; †p<0.05 vs OVX+E2 group (for EM-652.HCl group only)), in (C) lipoprotein lipase activity (data expressed in ?U/g protein).
Figure 3:
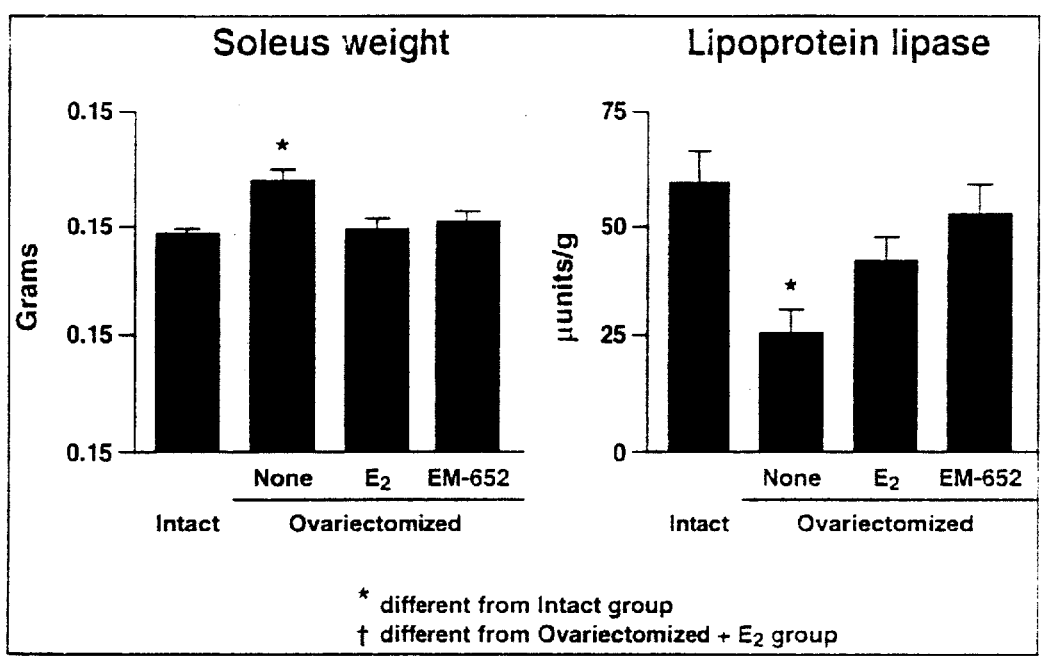

Brown adipose tissue is a major thermogenic effector in rodents. Ovariectomy showed a different pattern in interscapular brown adipose tissue than in white adipose tissue. The brown adipose tissue weight was 2-fold increased (FIG. 7A) as observed in white adipose tissue. However, the protein content (FIG. 7B) and the lipoprotein activity (FIG. 7C) were decreased by 33 and 30%, respectively, after OVX. On these three parameters, EM-652.HCl treatment completely reversed the effect of ovariectomy.

Weight of the soleus is usually a good index of the status of the protein mass of the organism. As expected, soleus weight, as shown in FIG. 8, was increased by Ovx (the increase in food intake results in an increase in energy deposition as both fat and protein). Both estradiol and EM-652.HCl treatments prevented the increase in muscle weight. Lipoprotein lipase in muscle is often positively associated with insulin sensitivity (the better the sensitivity, the more lipoprotein lipase in muscle). Ovx reduced lipoprotein lipase activity in the soleus, an indirect evidence of the development of insulin resistance in muscle. Both estradiol and EM-652.HCl treatments prevented the decrease in muscle lipoprotein lipase.

| | | Energy balance | | |
|---|---|---|---|---|
| Ovary status | Intact | | OVX | |
| Treatment | | None | E2 | EM-652 |
| Digestible energy intake (kJ) | 4708 | 6758[a] | 5511[a] | 4479[b] |
| Enegery gain (kJ) | 532 | 1677[a] | 903 | 278[b] |
| Apparent energy (kJ) | 4176 | 5081[a] | 4609[a] | 4201[b] |
| Food efficiency (%) | 10.2 | 24.1[a] | 15.9 | 5.9[b] |

[a]Different from Intact, p < 0.05
[b]Different from Ovariectomized + E2, p < 0.05.

Digestible energy intake is the total amount of energy ingested during a 20-day treatment (takes into account nondigestible matter such as fiber).

Energy gain is the amount of kilojoules deposited as fat+protein throughout the 20-day treatment.

Apparent energy expenditure is the amount of energy expended for metabolic needs and locomotion (calculated from energy intake and energy gain). Expected to be greater when lean mass is larger (such as Ovx animals).

Food efficiency is the efficiency with which ingested energy is deposited as fat and protein (in kJ deposited per 100 kJ ingested).

Example 4

Example of synthesis of the preferred compound of the invention.

Synthesis of (S)-(+)-7-hydroxy-3-(4'-hydroxyphenyl)-4-methyl-2-(4"-(2'"-piperidino-ethoxy)phenyl)-2H-1-benzopyran hydrochloride EM-01538 (EM-652, HCl)

Step A: BF3.Et2O, toluene; 100° C.; 1 hour.

Step C: 3,4-dihydropyran, p-toluenesulfonic acid monohydrate, ethyl acetate; 25° C. under nitrogen, 16 hours, and then crystallization in isopropanol.

Steps D, E, and F:
(1) piperidine, toluene, Dean & Stark apparatus, reflux under nitrogen;
(2) 1,8-diazabicyclo[5, 4, 0]undec-7-ene, DMF, reflux 3 hours;
(3) CH3MgCl, THF, −20 to 0° C. and then room temperature for 24 hours;

Steps G, H: (1S)-(+)-10-camphorsulfonic acid, acetone, water, toluene, room temperature, 48 hours.

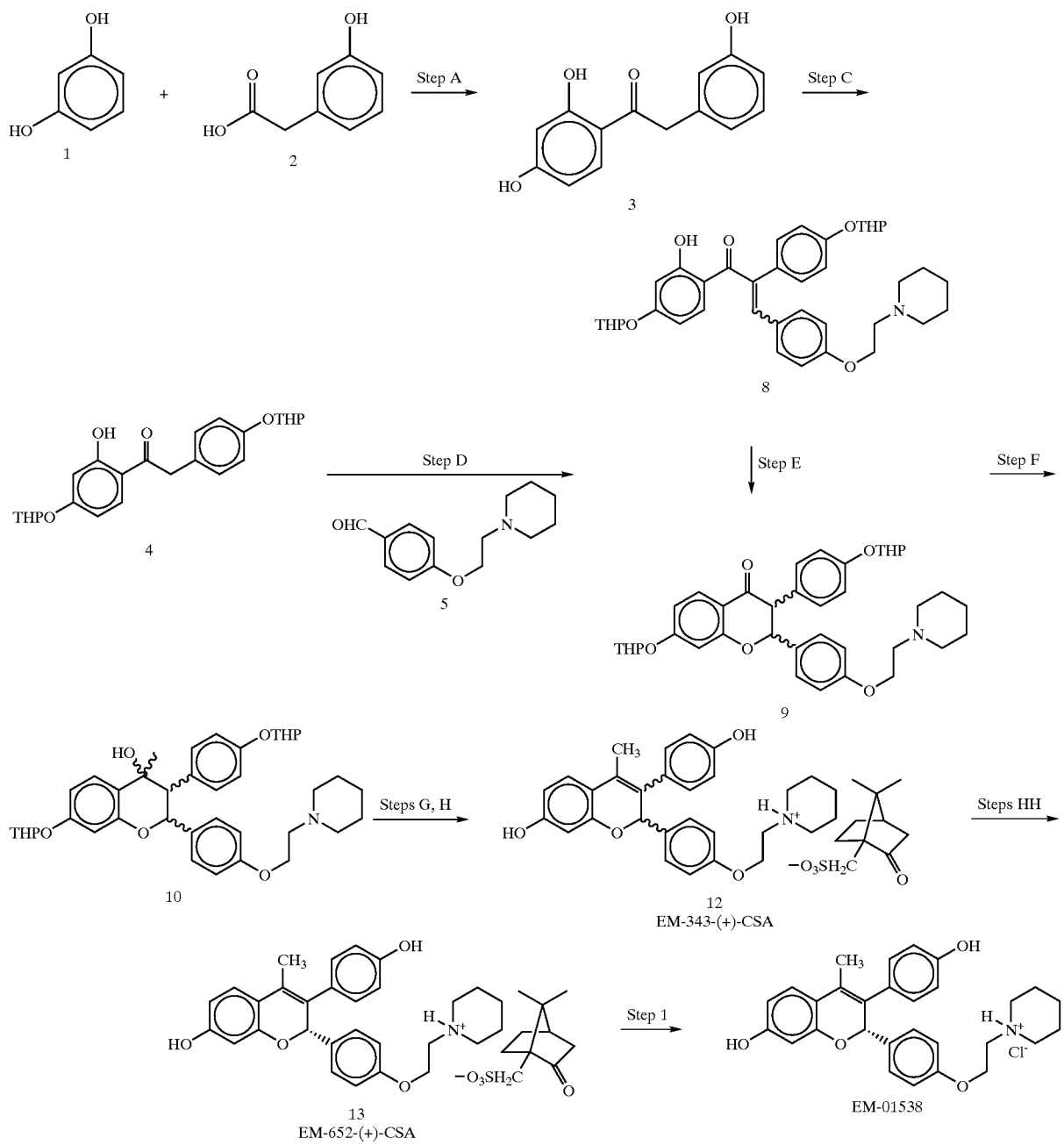

Step HH: 95% ethanol, 70° C., then room temperature 3 days.

Step HHR: Recycling of mother liquor and wash of step HH(S)-10-camphorsulfonic acid, reflux; 36 hours, then room temperature for 16 hours.

Step I:
(1) DMF aq., Na2CO3, ethyl acetate;
(2) ethanol, dilute HCl;
(3) water.

Synthesis of 2-tetrahydropyranyloxy-4-hydroxy-2'-(4"-tetrahydro-pyranyloxy-phenyl)acetophenone (4)

A suspension of 2,4-dihydroxy-2'-(4"-hydroxyphenyl) acetophenone 3 (97.6 g, 0.4 mole) (available from Chemsyn Science Laboratories, Lenexa, Kans.) in 3,4-dihydropyran (218 ml, 3.39 mole) and ethyl acetate (520 ml) was treated with p-toluenesulfonic acid monohydrate (0.03 g, 0.158 mmole) at about 25° C. The reaction mixture was stirred under nitrogen with no external heating for about 16 hours. The mixture was then washed with a solution of sodium bicarbonate (1 g) and sodium chloride (5 g) in water (100 ml). The phases were separated and the organic phase was washed with brine (20 ml). Each wash was back extracted with 50 ml ethyl acetate. All the organic phases were combined and filtered through sodium sulfate.

Solvent (about 600 ml) was removed by distillation at atmospheric pressure and isopropanol (250 ml) was added. Additional solvent (about 300 ml) was distilled at atmospheric pressure and isopropanol (250 ml) was added. Additional solvent (about 275 ml) was distilled at atmospheric pressure and isopropanol (250 ml) was added. The solution was cooled at about 25° C. with stirring and after about 12 hours, the crystalline solid was filtered, washed with isopropanol and dried (116.5 g, 70%).

Synthesis of 4-hydroxy-4-methyl-2-(4'-[2"-piperidino]-ethoxy)phenyl-3-(4'''-tetra-hydropyranyloxy)phenyl-7-tetrahydropyranyloxy-chromane (10)

A solution of 2-tetrahydropyranyloxy-4-hydroxy-2'-(4"-tetrahydropyranyloxyphenyl)acetophenone 4 (1 kg, 2.42 mole), 4-[2-(1-piperidino)ethoxy]benzaldehyde 5 (594 g, 2.55 mole) (available from Chemsyn Science Laboratories, Lenexa, Kans.) and piperidine (82.4 g, 0.97 mole) (available from Aldrich Chemical Company Inc., Milwaukee, Wis.) in toluene (8 L) was refluxed under nitrogen with a Dean & Stark apparatus until one equivalent of water (44 mL) was collected.

Toluene (6.5 L) was removed from the solution by distillation at atmospheric pressure. Dimethylformamide (6.5 L) and 1,8-diazabicyclo[5,4,0]undec-7-ene (110.5 g, 0.726 mole) were added. The solution was agitated for about 8 hours at room temperature to isomerize the chalcone 8 to chromanone 9 and then added to a mixture of water and ice (8 L) and toluene (4 L). The phases were separated and the toluene layer washed with water (5 L). The combined aqueous washes were extracted with toluene (3×4 L). The combined toluene extracts were finally washed with brine (3×4 L), concentrated at atmospheric pressure to 5.5 L and then cooled to −10° C.

With continued external cooling and stirring under nitrogen, a 3M solution of methylmagnesium chloride in THF (2.5 L, 7.5 mole) (available from Aldrich Chemical Company Inc., Milwaukee, Wis.) was added, maintaining the temperature below 0° C. After all the Grignard reagent was added, the external cooling was removed and the mixture allowed warm to room temperature. The mixture was stirred at this temperature for about 24 hours.

The mixture was again cooled to about −20° C. and with continued external cooling and stirring, saturated ammonium chloride solution (200 ml) was added slowly, maintaining the temperature below 20° C. The mixture was stirred for 2 hours and then added the saturated ammonium chloride solution (2 L) and toluene (4 L) and agitated for five minutes. The phases were separated and the aqueous layer extracted with toluene (2×4 L). The combined toluene extracts were washed with dilute hydrochloric acid until the solution became homogenous and then with brine (3×4 L). The toluene solution was finally concentrated at atmospheric pressure to 2 L. This solution was used directly in the next step.

Synthesis of (2R,S)-7-hydroxy-3-(4'-hydroxyphenyl)-4-methyl-2-(4"-[2'''-piperidino]ethoxy)phenyl)-2H-1-benzopyran (1S)-10-camphorsulphonic acid salt (±12)

To the toluene solution of 4-hydroxy-4-methyl-2-(4'-[-2"-piperidino]-ethoxy)phenyl-3-(4'''-tetrahydropyranyloxy) phenyl-7-tetrahydropyranyloxychromane (10) was added acetone (6 L), water (0.3 L) and (S)-10-camphorsulphonic acid (561 g, 2.42 mole) (available from Aldrich Chemical Company Inc., Milwaukee, Wis.). The mixture was agitated under nitrogen for 48 hours after which time the solid (2R,S)-7-hydroxy-3-(4'-hydroxyphenyl)-4-methyl-2-(4"-[2'''-piperidino]ethoxy)phenyl)-2H-1-benzopyran (1S)-10-camphorsulphonic acid salt (12) was filtered, washed with acetone and dried (883 g). This material was used in the next (HH) step without further purification.

Synthesis of (2S)-7-hydroxy-3-(4'-hydroxyphenyl)-4-methyl-2-(4'-[2'''-piperidino]ethoxy)phenyl)-2H-1-benzopyran (1S)-10-camphorsulphonic acid salt (13, (+)-EM-652(1S)-CSA salt)

A suspension of (2R,S)-7-hydroxy-3-(4'-hydroxyphenyl)-4-methyl-2-(4"-[2'''-piperidino]ethoxy)phenyl)-2H-benzopyran (1S)-10-camphorsulphonic acid salt±12 (759 g) in 95% ethanol was heated with stirring to about 70° C. until the solid had dissolved. The solution was allowed to cool to room temperature with stirring then seeded with a few crystals of (2S)-7-hydroxy-3-(4'-hydroxyphenyl)-4-methyl-2-(4"-[2'''-piperidino]ethoxy)phenyl)-2H-1-benzopyran (1S)-10-camphor-sulphonic acid salt 13. The solution was stirred at room temperature for about three days in total. The crystals were filtered, washed with 95% ethanol and dried (291 g, 76%). The de of the product was 94.2% and the purity 98.8%.

Synthesis of (S)-(+)-7-hydroxy-3-(4'-hydroxyphenyl)-4-methyl-2-(4"-(2'''-piperidinoethoxy)phenyl)-2H-1-benzopyran hydrochloride EM-01538 (EM-652,HCl)

A suspension of compound 13 (EM-652-(+)-CSA salt, 500 mg, 0.726 mmol) in dimethylformamide (11 µL, 0.15 mmol) was treated with an 0.5 M aqueous sodium carbonate solution (7.0 mL, 3.6 mmol), and stirred for 15 min. The suspension was treated with ethyl acetate (7.0 mL) and stirred during 4 h. The organic phase was then washed with an aqueous saturated sodium carbonate solution (2×5 mL) and brine (1×5 mL) dried over magnesium sulfate, and concentrated. A solution of the resulting pink foam (EM-652) in ethanol (2 mL) was treated with 2 N hydrochloric acid (400 µL, 0.80 mmol), stirred for 1 h, treated with distilled water (5 mL), and stirred during 30 min. The resulting suspension was filtered, washed with distilled water (5 mL), dried in air and under high vacuum (65° C.) to give a creamy powder (276 mg, 77%): Fine off-white powder; Scanning Calorimetry: Melting peak onset at 219° C., DH=83 J/g; [a]24D=154° in methanol 10 mg/ml. ;1H NMR (300 MHz, CD3OD) d(ppm) 1.6 (broad, 2H, H-4'''), 1.85 (broad, 4H, H-3'''' and 5''''), 2.03 (s, 3H, CH3), 3.0 and 3.45 (broad, 4H, H-2'''' and 6''''), 3.47 (t, J=4.9 Hz. 2H, H-3'''), 4.26 (t, J=4.9 Hz, 2H, H-2'''), 5.82 (s, 1H, H-2), 6.10

(d, J=2.3 Hz, 1H, H-8), 6.35 (dd, J=8.4, 2.43 Hz, 1H, H-6), 6.70 (d, J=8.6 Hz, 2H, H-3', and H-5'), 6.83 (d, J=8.7 Hz, 2H, H-3" and H-5"), 7.01 (d, J=8.5 Hz, 2H, H-2' and H-6'), 7.12 (d, J=8.4 Hz, 1H, H-5), 7.24 (d, J=8.6 Hz, 2H, H-2" and H-6"); 13C RMN (CD3OD, 75 MHz) d ppm 14.84, 22.50, 23.99, 54.78, 57.03, 62.97, 81.22, 104.38, 109.11, 115.35, 116.01, 118.68, 125.78, 126.33, 130.26, 130.72, 131.29, 131.59, 134.26, 154.42, 157.56, 158.96, 159.33. Elemental Composition: C, H, N, Cl: Theory; 70.51, 6.53, 2.84, 7.18, %, Found: 70.31, 6.75, 2.65, 6.89%.

Example 5 shows the prevention of the LHRH-A-induced fat increase by EM-652.HCl, a compound of the invention, alone or in combination with DHEA, a sex hormone precursor, in intact female rats. It can be seen that 6-month LHRH-A treatment increases significantly by 58% the percentage of body fat of intact female rats, while with concomitant administration of EM-652.HCl or DHEA, this increment was only of 35% and 19%, respectively. With the combination of both drugs, no fat increase was observed following LHRH-A treatment.

In Example 6, the prevention of obesity in female rats over a 20-day period is presented. Ovariectomy increases the percentage of total body fat and weight of retroperitoneal adipose tissue by 20% and 68%, respectively. These increments are prevented and even body fat and retroperitoneal adipose tissue are decreased by the administration of EM-652.HCl, estradiol, DHEA, or combinations of EM-652.HCl and DHEA or EM-652.HCl and estradiol of 46%, 46%, 59%, 56%, and 45%, respectively, for body fat and by 59%, 78%, 75%, 69%, and 68%, respectively for retroperitoneal adipose tissue. A similar experiment is presented in Example 7. In this case, prevention of obesity is followed during 34-weeks and then the percentages of body fat and retroperitoneal adipose tissue are approximatively 60% increased by ovariectomy. This increment is prevented by administration of ethynyl estradiol, Raloxifene (EM-1105), EM-652.HCl (EM-1538), DHEA, or the combination of EM-652.HCl and DHEA.

Examples 8A (male) and 8B (female) report data of the effectiveness of the invention in the prevention as well as in the treatment of obesity. To lean and obese Zucker male and female rats were administered 2.5 mg/kg/day of EM-652.HCl for 20 days. The model of prevention is represented by lean rats while the model of treatment of obesity is represented by already obese rats. The data on body weight gain, lipoprotein lipase activity in white retroperitoneal adipose tissue and soleus muscle as well as plasma concentrations of insulin, glucose, total cholesterol, and triglycerides are reported in table 7 for male and table 8 for female animals (see Example 3 for significance of these parameters).

The antiestrogen EM-652.HCl decreased significantly body weight gain by 38% for lean male rats and 35% for obese male rats while lipoprotein lipase activity in white retroperitoneal adipose tissue and soleus muscle is not modified in both sexes. Plasma insulin is reduced by 35%, 57%, and 48% in lean males, obese males and lean females, respectively, while in obese females which show a much high level of insulin, EM-652.HCl has no significant effect. Plasma cholesterol which is higher in the obese group is also reduced by EM-652.HCl administration. Serum glucose is not affected by EM-652.HCl treatment.

In Example 9 the effect of EM-652.HCl, DHEA or combination of both on intact or ovariectomized female rats receiving a rich diet in sucrose and fat is reported on total weight, weight and lipoprotein lipase activity of white inguinal and retroperitoneal adipose tissue, of brown adipose tissue, of soleus muscle and vastus lateralis muscle (VLM). Plasma insulin, glucose, total cholesterol, triglycerides, and leptin as well as hepatic cholesterol and triglycerides are also reported.

Example 10 reports the effect on weight gain and on lipid-lipoprotein metabolism in rats following treatment with different selective estrogen receptor modulators described in the literature ERA-923, Lasofoxifene, LY 353381 and Raloxifene) as well as with EM-652.HCl, the preferred compound of the invention. Tested compounds were administered by oral gavage for 20 days (0.5 mg/rat for each compound) in 0.4% methylcellulose to ovariectomized female rats. Intact control, ovariectomized (OVX) control and OVX rats treated with 17-estradiol (E2) were used as reference. The body weight and the food consumption which are increased by ovariectomy are significantly decreased by the treatment with the tested compounds at the level observed in intact controls. Weight and lipoprotein lipase activity of white inguinal and retroperitonal adipose tissue are diminished by the above treatment (except for ERA-923 and LY 353381 for white adipose inguinal tissue and ERA-923 and Lasofoxifene for lipoprotein lipase activity of inguinal tissue) while brown adipose tissue and muscle do not seem significantly affected. It can be seen that all tested compounds lower significantly the serum concentration of cholesterol and triglycerides but have no effect on glucose levels. Serum insulin was decreased by treatment of OVX rats with EM-652.HCl, ERA-923, Lasofoxifene, LY 353381, and Raloxifene.

In Examples 11 and 12, the in vitro efficiency in estrogen dependant cell lines of known antiestrogens and compounds of the invention are reported. The effect of antiestrogens on alkaline phosphatase activity in human endometrial adenocarcinoma Ishikawa cells is shown in table 11 of Example 10. The antiestrogenic activity is reported in the last column as IC 50 expressed in nM of the inhibition of 1 nM E2 stimulated alkaline phosphatase while the intrinsic estrogenic activity of the tested compounds is reported in the penultimate column as percentage of 1 nM E2 stimulation of alkaline phosphatase activity. It can be seen that the most active antiestrogens are EM-652.HCl, LY 353381, Raloxifene, Lasofoxifene, and ERA-923. The others are at least ten times less active. However, among the best active compounds, some possess a significant residual unwanted estrogenic activity: LY 353381(16%), Lasofoxifene (18%), and Raloxifene (13%). Thus, the present data indicates that compounds EM-652.HCl and ERA-923 do not show significant estrogenic activity in Ishikawa cells. In Example 12 a comparison between EM-652.HCl, our preferred compound, and ERA-923 in human breast cancer MCF-7 cells shows the advantage of EM-652.HCl. Thus, it is more than four times more active than ERA-923 as antiestrogen (EC50 of inhibition of 0.8 nM versus 3.7 nM) (table 12).

In Example 13, the effect of 20 day-treatment with EM-652.HCl, TSE 424 or Lasofoxifene on body weight, retroperitoneal adipose tissue, uterine weight and cholesterol levels was evaluated in ovariectomized female rats fed with a commercial rodent diet. Ovariectomy induced 17% and 19% increases in total body weight and retroperitoneal fat tissue weight, respectively, while the administration of 0.5 mg of EM-652.HCl, TSE 424 or Lasofoxifene prevented body weight increase by 64%, 59% and 127%, respectively, and led to adipose tissue weight values below those observed in intact control animals for all compounds studied. The administration of EM-652.HCl and TSE 424 had no effect on uterine weight compared to the OVX control animals. However, the administration of 0.5 mg of Lasofoxifene caused a 62% increase (p>0.01) of uterine weight that was completely reversed by the simultaneous administration of 2.5 mg of EM-652.HCl, thus suggesting an estrogenic activity of Lasofoxifene. Finally, the OVX-induced increase in total serum cholesterol levels was completely prevented by the administration of EM-652. HCl, TSE 424 and Lasofoxifene and led to cholesterol values significantly lower than those observed in intact control animals.

Example 5

Effect on fat accumulation by treatment with EM-652.HCl and DHEA, administered alone or in combination, to intact female rats receiving or not a LHRH-A.

URMA-r-04-99

The objective of this study is to determine the effect on fat of treatment with EM-652.HCl and dehydroepiandrosterone (DHEA) in intact female rats receiving or not a luteinizing hormone releasing hormone agonist (LHRH-A, LHRH ethylamide diacetate). For this purpose, intact female rats, treated or not with LHRH-A (2 µg/rat), received daily administration of EM-652.HCl (2.5 mg/kg) and DHEA (100 mg/kg), alone or in combination, for 6 months. EM-652.HCl was administered orally, DHEA was applied topically while LHRH-A was injected subcutaneously. All treatments were administered once daily.

Test Animal

Species: *Rattus norvegicus*

Strain: Sprague-Dawley Rat (Crl :CD® (SD) BR VAF/PlusTM)

Sex: Female

Age: At onset of dosing, rats were approximately 10 to 12-week old.

Housing and maintenance a) Housing:
The rats were housed individually in stainless steel cages during the acclimation and study periods.

b) Temperature and Humidity:
Environmental conditions (temperature, humidity) in the rat room were recorded continuously using a computerized automated system.
The targeted conditions were of 22±C and 50±20% relative humidity.

c) Light-Dark Cycle:
The photoperiod were 12 hours of light and 12 hours of darkness. These parameters were recorded continuously using a validated computerized automated system. Lights were on from 07:15 to 19:15.

d) Diet:
Certified Rodent feed (Lab Diet # 5002, pellets) and tap water were provided ad libitum.

Randomization:
Rats were assigned to each group at random during the acclimation period.

Methods and Experimental Design

Test Groups

One hundred twenty rats were separated into 8 groups of 15 animals for conduct of the study outlined below:

| Treatment | Dosing suspensions administered orally | | Dosing solutions applied topically | | LHRH-A (Injected sc) |
|---|---|---|---|---|---|
| | Dose (mg/kg) | Vol./rat (ml) | Dose (mg/kg) | Vol./rat (ml) | Dose 2 µg/rat |
| INTACT | — | 0.5 | — | 0.5 | — |
| EM-652.HCl | 2.5 | 0.5 | — | 0.5 | — |
| DHEA | — | 0.5 | 100 | 0.5 | — |
| DHEA + EM-652.HCl | 2.5 | 0.5 | 100 | 0.5 | — |
| OHRH-A | — | 0.5 | — | 0.5 | 0.5 ml |
| LHRH-A + EM-652.HCl | 2.5 | 0.5 | — | 0.5 | 0.5 ml |
| LHRH-A + DHEA | — | 0.5 | 100 | 0.5 | 0.5 ml |
| LHRH-A + DHEA + EM-652.HCl | 2.5 | 0.5 | 100 | 0.5 | 0.5 ml |

Preparation of Test Articles

The LHRH-A is available in solution at a concentration of 1.0 mg/ml. We diluted this concentrated solution (in order to obtain a final concentration of 0.002 mg/ml) by using the following vehicle: 0.3% Sodium Chloride and 0.25% Sodium Phosphate monobasic, monohydrate in water. The sodium hydroxide (aqueous) was used to adjust the pH between 5.6–6.2.

Dosing suspensions/solutions were prepared every two weeks according to the most recent body weight (group mean) except for the LHRH-A solution. For EM-652.HCl administered orally, the vehicle (0.4% methylcellulose) was added to the tested compound, previously weighed into a glass bottle, at least 48 hours prior to the first dosing day. To ensure the homogeneity of dosing suspension, it was stirred at least 48 hours at 2 to 8 C. Dosing suspension was kept at 2 to 8 C. For DHEA solution applied topically, the ethanol was added to DHEA and the mix were agitated until dissolution of DHEA. Then, the polypropylene glycol were added and the solution agitated until homogeneity. Dosing solution was kept at 2 to 8 C. For LHRH-A solution injected subcutaneously, a dilution of the concentrated solution using the appropriate vehicle was prepared every month. Dosing solution was kept at 2 to 8 C.

Animal Preparation

Prior to the first dose day and as needed during the study, a portion of dorsal skin (approximately 5×5 cm) was shaved for the topical application of DHEA.

Dosing

The administration of tested compounds or vehicle was given from on Study Day 1 of the protocol. The tested compounds were given as suspension in 0.4% methylcellulose by oral gavage (0.5 ml/gavage/rat) once daily or were applied topically in 50% ethanol-50% propylene glycol (0.5 ml/application/rat) once daily. Rats from groups 5 to 8 received also the LHRH-A once daily by subcutaneous injection (0.5 ml/injection/rat). Rats not receiving a tested compound orally and/or topically received the appropriate vehicle alone.

Measurement of Body Fat

Body composition was measured on whole skeleton of animal under Isoflurane-induced anesthesia using dual energy x-ray absorptiometry (DEXA; QDR 4500A, Hologic) during the acclimation period and after 6 months of treatment.

Results

TABLE 4

| TREATMENT | FAT (%) |
|---|---|
| INTACT | 23.1 ± 1.6 |
| EM-652.HCl | 19.1 ± 1.4 |
| DHEA | 20.2 ± 2.3 |
| DHEA + EM-652.HCl | 18.8 ± 1.3 |
| LHRH-A | 36.4 ± 2/2 |
| LHRH-A + EM-652.HCl | 31.2 ± 2.0 |
| LHRH-A + DHEA | 27.4 ± 2.1 |
| LHRH-A + DHEA + EM-652.HCl | 25.0 ± 1.7 |

Example 6
Effect of a 20-day treatment with EM-652.HCl, estradiol, and DHEA on body fat and body weight parameters in ovariectomized female rats.
URMA-r-27-00

The objective of this study was to evaluate the effect on body fat and body weight parameters of EM-652.HCl, estradiol and DHEA administered orally alone or in combination, to ovariectomized (OVX) female rats receiving an enriched carbonhydrate diet.

Test Animal

Species: *Rattus norvegicus*

Strain: Sprague-Dawley Rat (Crl: CD® (SD) BR VAF/PlusTM)

Sex: Female

Body Weight: At onset of dosing, body weights were approximately 200–250 g.

Housing and maintenance a) Housing: The rats were housed individually in stainless steel cages of conventional design during the acclimation and study periods.

b) Temperature and Humidity: Environmental conditions (temperature, humidity) in the rat room were recorded continuously using a computerized automated system. The targeted conditions were of 22±3 C. and 50±20% relative humidity.

c) Light-Dark Cycle: The photoperiod was 12 hours of light and 12 hours of darkness. These parameters were recorded continuously using a computerized automated system. Lights were on from 07:15 to 19:15.

d) Diet: Certified Rodent feed (Lab Diet # 5002, pellets) and tap water were provided ad libitum during the acclimation period. During the study period, the rats received an enriched carbonhydrate diet ad libitum. The enriched diet (diet #3) was composed of (g/100 g): Corn starch, 31.2; Dextrose, 31.2; Casein, 20.0; Corn oil, 6.4; dl-Methionine, 0.3; Vitamin mix, 1.0; AIN-76 mineral mix, 4.9; Fiber, 5.0.

The day prior to their necropsy, rats were fasted (with access to water only) at the end of the afternoon (around 16h00).

Randomization:

Rats were assigned to each group at random on day 0 of the study.

Methods and Experimental Design

Test Groups 80 rats were assigned to 8 groups of 10 rats for the conduct of the study outlined below:

| Treatment | Dosing suspensions | |
|---|---|---|
| | Dose (mg/rat) | Vol./rat (ml) |
| Intact | 0 | 0.5 ml |
| OVX | 0 | 0.5 ml |
| OVX + EM-652.HCl | 0.5 | 0.5 ml |
| OVX + E | 0.5 | 0.5 ml |
| OVX + DHEA | 100 | 0.5 ml |
| OVX + EM-652.HCl + DHEA | 0.5 + 100 | 0.5 ml + 0.5 ml |
| OVX + EM-652.HCl + E | 0.5 + 100 | 0.5 ml + 0.5 ml |

Animal Preparation

On day 0 of the study, rats from groups 2 to 8 were ovariectomized, by bilateral flank incision, under Isoflurane-induced anesthesia. Rats from group 1 were sham-operated.

Dosing

The administration of the test articles or vehicle began on Day 1 (the day following the ovariectomy). The tested compounds were given as suspensions in 0.4% methylcellulose by oral gavage (0.5 ml/gavage) for 20 days.

Measurement of Body Composition

On day 21 of the study (prior to the necropsy), body composition was determined on whole body skeleton of animals under Isoflurane-induced anesthesia using dual energy x-ray absorptiometry (DEXA; QDR 4500A, Hologic) in order to determine the effect of treatments on fat percentage.

Organs and Tissues Collected

Right and left retroperitoneal adipose tissue were collected and weighed.

Results

TABLE 5

| Treatment | Fat % | Retroperitoneal adipose tissue g |
|---|---|---|
| Intact | 15.7 ± 0.8 | 2.20 ± 0.20 |
| OVX | 18.9 ± 1.5 | 3.70 ± 0.41 |
| OVX + EM-652.HCl | 10.2 ± 1.2 | 1.52 ± 0.18 |
| OVX + $E_2$ | 10.3 ± 0.6 | 0.81 ± 0.17 |
| OVX + DHEA | 7.8 ± 0.8 | 0.92 ± 0.17 |
| OVX + EM-652.HCl + DHEA | 8.4 ± 0.9 | 1.15 ± 0.17 |
| OVX + EM-652.HCl + $E_2$ | 10.4 ± 0.7 | 1.17 ± 0.19 |

Example 7
Effect of a 34-week treatment with ethynyl estradiol, EM-652.HCl, Raloxifene, and DHEA on body fat and body weight parameters in ovariectomized female rats.
URMA-r-42-98

The objective of this study was to assess the effect of a combined treatment with EM-652.HCl, and DHEA on body fat and body weight parameters in ovariectomized rats. For this purpose, ovariectomized rats received daily administration of EM-652.HCl (1 mg/kg), and DHEA (80 mg/kg) alone or in combinaison, for 34 weeks. EM-652.HCl was administered orally while DHEA was applied topically on dorsal skin. One group of animals was orally treated with 17-ethynylestradiol (0.1 mg/kg) and Raloxifene (EM-1105; 1 mg/kg) for comparison.

Materials and Methods

Animals and Treatment

Ten to twelve week-old female Sprague-Dawley rats (Crl:CD(SD)Br) weighing approximately 235–250 g at start of treatment were used. Eighty rats were randomly distributed between 7 groups of 11 to 12 animals per group as follows: 1) Intact control; 2) OVX control; 3) OVX+EE2 (0.1 mg/kg); 4) OVX+raloxifene (1 mg/kg); 5) OVX+EM-652.HCl (1 mg/kg); 6) OVX+DHEA (80 mg/kg); 7) OVX+ EM-652.HCl+DHEA. On day 1 of the study, the animals of the appropriate groups were bilaterally ovariectomized (OVX) under isoflurane anesthesia. EM-652.HCl, raloxifene and EE2 (Steraloids) were administered once daily by oral gavage as suspension in 0.4% methylcellulose (0.5 ml/rat) for 34 weeks while DHEA was applied topically once daily on dorsal skin as a solution in 50% ethanol-50% propylene glycol (0.5 ml/rat) for the same time period. Approximately 24 hours after the last dosing, overnight fasted animals were killed by exsanguination at the abdominal aorta under isoflurane anesthesia Left and right retroperitoneal adipose tissues were collected and weighed.

Measurement of Body Composition

After 34 weeks of treatment, individual rats under anesthesia with isoflurane had their whole body skeleton scanned using dual energy x-ray absorptiometry (DEXA; QDR 4500A, Hologic, Waltham, Mass.) and a Regional High Resolution Scan software. The body composition (including fat percentage) was determined.

Statistical Analyses

Data were expressed as the means±SEM.

Results

TABLE 6

| Treatment | Right retroperitoneal adipose tissue g | Left retroperitoneal adipose tissue g | Fat % |
|---|---|---|---|
| Intact control | 1.43 ± 0.12 | 1.80 ± 0.26 | 25.7 ± 2.5 |
| OVX control | 2.53 ± 0.24 | 2.64 ± 0.18 | 42.1 ± 1.5 |
| OVX + EE$_2$ | 1.29 ± 0.22 | 1.15 ± 0.18 | 19.8 ± 1.9 |
| (0.1 mg/kg) OVX + Raloxifene | 1.29 ± 0.12 | 1.41 ± 0.13 | 22.8 ± 1.6 |
| (1 mg/kg) OVX + EM-652.HCl | 2.07 ± 0.18 | 2.19 ± 0.28 | 27.7 ± 1.8 |
| (1 mg/kg) OVX + DHEA | 2.16 ± 0.25 | 1.98 ± 0.17 | 26.8 ± 2.3 |
| (80 mg/kg) OVX + EM-652.HCl + DHEA | 1.62 ± 0.18 | 1.47 ± 0.18 | 25.1 ± 1.8 |

Example 8A

Effect of EM-652.HCl on energy balance and lipid-lipoprotein metabolism in lean and obese Zucker male rats. URMA-r-61-99

The objective of this study was to determine the effect of EM-652.HCl on energy balance and lipid-lipoprotein metabolism in lean and obese Zucker male rats. For this purpose, EM-652.HCl (2.5 mg/kg) was administered orally (gavage) once daily for 14 days to intact lean and obese Zucker male rats.

Test Animal
  Species: *Rattus norvegicus*
  Strain: Zucker
  Sex: male
  Body Weight: At onset of dosing, body weights were approximately: lean rats:175±15 g; obese rats: 235±15 g Acclimation Rats were acclimatized to laboratory conditions at least five days prior the beginning of the experiment.

Housing and maintenance
  a) Housing: The rats were housed individually in stainless steel cages of conventional design during the acclimation and study periods.
  b) Temperature: Temperature in the rat room was recorded once daily. The targeted temperature was 22±3 C.
  c) Light-Dark Cycle: The photoperiod was 10 hours of light and 14 hours of darkness. Lights were opened at 07:00, and closed at 17h00.
  d) Diet: During the acclimation period, rats received a commercial rodent diet (Purina, # 5075) and tap water ad libitum. During study period, rats received the following diet (diet # 3) composed of (g/100 g): Starch, 31.2; Dextrose, 31.2; Casein, 20.0; Corn oil, 6.4; dl-Methionine, 0.3; Vitamin mix, 1.0; AIN-76 mineral mix, 4.9; Fiber, 5.0.

Rats were fasted (with access to water only) around 07h00 the morning of their necropsy day.

Randomization:

One day prior to the first dosing day, rats were weighed and assigned to each group in order to have groups with equivalent mean body weights.

Methods and Experimental Design

Test Groups

Sixteen lean and sixteen obese intact male rats were assigned to 4 groups of 8 rats for conduct of the study outlined below

| Nb of rat group | Rat status | Treatment | Dose (mg/kg) |
|---|---|---|---|
| 8 | Lean | EM-652.HCl | 2.5 |
| 8 | Obese | EM-652.HCl | 2.5 |
| 8 | Lean | CONTROL | 0 |
| 8 | Obese | CONTROL | 0 |

Dosing

Administration of the tested compound or vehicle started on Day 1 of the study. The tested compound EM-652.HCl was given as suspension in 0.4% methylcellulose by oral gavage (0.5 ml/gavage/rat) once daily for 14 days. Rats from control groups received the vehicle alone (0.5 ml/gavage/rat) for the same time period.

Body Weights

During the acclimation period, animals were weighed one day prior to the start of dosing for randomization. Then, rats were weighed on the first dosing day and every 2 days thereafter as well as on the day of necropsy. Body weights were recorded with a precision of 1 g.

Food Consumption

Food consumption was evaluated every 2 days during the study period.

Method of Sacrifice

Following an approximative 6-hour fasting period, animals were necropsied (approximately 30 hours after the last dosing). They were anesthesized with ketamine-xylazine and blood drawn by cardiac punction.

Blood Samples

Blood lipids (Total cholesterol (CHOL) and Triglycerides (TG)) and glucose were measured on frozen plasma samples using the Boehringer Mannheim Diagnostic Hitachi 911 Analyzer (Boehringer Mannheim Diagnostic Laboratory Systems). Circulating hormones and substrates (Leptin, Insulin) were measured on frozen plasma samples with the following kits:
  Leptin: Linco RIA kit
  Insulin: Linco RIA kit Organs and Tissues Collected The retroperitoneal adipose tissue and the soleus (muscle) were collected and frozen in liquid nitrogen for further determination of lipoprotein lipase (LPL) activity.

TABLE 7

| | | | Lipoprotein lipase activity soleus $\mu$U/g | | | Plasma total cholesterol | Plasma triglycerides |
|---|---|---|---|---|---|---|---|
| GROUP | | Weight gain | Lipoprotein lipase activity White retroperitoneal | Plasma insulin | Plasma glucose | | |
| phenotype | treatment | g | $\mu$U/g protein | protein | nmol/L | mmol/L | mmol/L | mmol/L |
| Lean | control | 73.0 ± 4.2 | 2066 ± 353 | 71.7 ± 7.9 | 0.095 ± 0.025 | 10.74 ± 0.87 | 2.10 ± 0.15 | 1.47 ± 0.20 |
| Lean | EM-652.HCl 2.5 mg/kg | 44.9 ± 3.5 | 1701 ± 348 | 69.5 ± 8.4 | 0.062 ± 0.005 | 9.35 ± 0.51 | 1.18 ± 0.09 | 1.52 ± 0.13 |
| Obese | control | 110.5 ± 6.7 | 7233 ± 511 | 51.9 ± 8.8 | 1.092 ± 0.369 | 11.06 ± 0.84 | 5.07 ± 0.28 | 4.21 ± 0.78 |
| Obese | EM-652.HCl 2.5 mg/kg | 71.6 ± 3.3 | 7046 ± 1185 | 58.1 ± 4.6 | 0.475 ± 0.087 | 11.84 ± 0.62 | 2.28 ± 0.25 | 7.16 ± 1.06 |

Example 8B

Effect of EM-652.HCl on energy balance and lipid-lipoprotein metabolism in lean and obese Zucker female rats.

URMA-r-47-99

The objective of this study was to determine the effect of EM-652.HCl on energy balance and lipid-lipoprotein metabolism in lean and obese Zucker female rats. For this purpose, EM-652.HCl (2.5 mg/kg) was administered orally (gavage) once daily for 14 days to intact lean and obese Zucker female rats.

Test Animal Specifications

Species: *Rattus norvegicus*
Strain: Zucker
Sex: female
Body Weight: At onset of dosing, body weights were approximately: lean rats: 114±2 g; obese rats: 182±6 g Acclimation Rats were acclimatized to laboratory conditions at least five days prior the beginning of the experiment.

Housing and maintenance a) Housing:
   The rats were housed individually in stainless steel cages of conventional design during the acclimation and study periods.
b) Temperature:
   Temperature in the rat room was recorded once daily. The targeted temperature was 22±3° C.
c) Light-Dark Cycle:
   The photoperiod was 10 hours of light and 14 hours of darkness.
   Lights were opened at 07:00, and closed at 17h00.
d) Diet:
   During the acclimation period, rats received a commercial rodent diet (Purina, # 5075) and tap water ad libitum. During study period, rats received the following diet (diet # 3) composed of (g/100 g): Starch, 31.2; Dextrose, 31.2; Casein, 20.0; Corn oil, 6.4; dl-Methionine, 0.3; Vitamin mix, 1.0; AIN-76 mineral mix, 4.9; Fiber, 5.0. Rats were fasted (with access to water only) around 07h00 the morning of their necropsy day.

Randomization:

Two days prior to the first dosing day, rats were weighed and assigned to each group in order to have groups with equivalent mean body weights.

Methods and Experimental Design

Test Groups

Sixteen lean and sixteen obese intact female rats were assigned to 4 groups of 8 rats for conduct of the study outlined below.

| Nb of rat group | Rat status | Treatment | Dose (mg/kg) |
|---|---|---|---|
| 8 | Lean | EM-652.HCl | 2.5 |
| 8 | Obese | EM-652.HCl | 2.5 |
| 8 | Lean | CONTROL | 0 |
| 8 | Obese | CONTROL | 0 |

Dosing

Administration of the tested compound or vehicle started on Day 1 of the study. The tested compound EM-652.HCl was given as suspension in 0.4% methylcellulose by oral gavage (0.5 ml/gavage/rat) once daily for 14 days. Rats from control groups received the vehicle alone (0.5 ml/gavage/rat) for the same time period.

Body Weights

During the acclimation period, animals were weighed two days prior to the start of dosing for randomization. Then, rats were weighed on day 1 of the study and every 2 days during the study period as well as on the day of necropsy. Body weights were recorded with a precision of 1 g.

Food Consumption

Food consumption was evaluated every 2 days during the study period.

Method of Sacrifice

Following an approximative 6-hour fasting period, animals were necropsied (approximately 30 hours after the last dosing). They were anesthesized with ketamine-xylazine and blood drawn by cardiac punction.

Blood Samples

Blood lipids (Total cholesterol (CHOL) and Triglycerides (TG)) and glucose were measured on frozen plasma samples using the Boehringer Mannheim Diagnostic Hitachi 911 Analyzer (Boehringer Mannheim Diagnostic Laboratory Systems). Circulating hormones and substrates (Leptin, Insulin, corticosterone) were measured on frozen plasma samples with the following kits:

Leptin: Linco RIA kit
Insulin: Linco RIA kit

Organs and Tissues Collected

The retroperitoneal adipose tissue and the soleus (muscle) were collected and frozen in liquid nitrogen for further determination of lipoprotein lipase (LPL) activity.

TABLE 8

| GROUP | | Weight | Lipoprotein lipase activity White retroperitoneal | Lipoprotein lipase activity soleus $\mu$U/g | Plasma insulin | Plasma glucose | Plasma total cholesterol | Plasma triglycerides |
|---|---|---|---|---|---|---|---|---|
| phenotype | treatment | (g) | $\mu$U/g protein | protein | nmol/L | mmol/L | mmol/L | mmol/L |
| Lean | control | 175 ± 4 | 1586 ± 155 | 55.8 ± 8.1 | 0.122 ± 0.022 | 9.45 ± 0.68 | 2.33 ± 0.10 | 1.25 ± 0.16 |
| Lean | EM-652.HCl 2.5 mg/kg | 154 ± 5 | 1349 ± 246 | 60.8 ± 11.1 | 0.063 ± 0.012 | 9.60 ± 0.41 | 1.57 ± 0.14 | 0.83 ± 0.07 |
| Obese | control | 313 ± 9 | 3980 ± 327 | 36.9 ± 8.6 | 0.410 ± 0.033 | 10.63 ± 0.55 | 4.83 ± 0.27 | 12.51 ± 3.25 |
| Obese | EM-652.HCl 2.5 mg/kg | 291 ± 9 | 3819 ± 485 | 36.6 ± 7.1 | 0.515 ± 0.091 | 11.70 ± 0.47 | 3.27 ± 0.97 | 22.20 ± 4.44 |

Example 9

Effects of EM-652.HCl and DHEA, administered alone or in combination, on energy balance and lipid-lipoprotein metabolism in rats.

URMA-r-03-99

The objective of this study was to determine the effects of EM-652.HCl and DHEA, administered alone or in combination, on energy balance and lipid-lipoprotein metabolism in rats. The effect of treatments was evaluated on many parameters following a 20-day treatment with EM-652.HCl (0.5 mg/rat, ~2.5 mg/kg, per os) and DHEA (20 mg/rat, ~100 mg/kg, topical application), administered alone or in combination, to intact (INT) and ovariectomized (OVX) female rats receiving a high sucrose-high fat diet. For comparison, one intact and ovariectomized control group received the enriched diet while other control animals (intact and OVX) received the commercial rodent diet.

Test Animal
Species: *Rattus norvegicus*
Strain: Sprague-Dawley Rat (Crl:CD® (SD) BR VAF/PlusTM)
Sex: Female
Body Weight: At onset of dosing, body weights were approximately 190–220 g.

Acclimation
Rats were acclimatized to laboratory conditions at least five days prior the beginning of the experiment.

Housing and maintenance
a) Housing:
The rats were housed individually in stainless steel cages of conventional design during the acclimation and study periods
b) Temperature:
Temperature in the rat room was recorded once daily. The targeted temperature was 22±3 C.
c) Light-Dark Cycle:
The photoperiod were 10 hours of light and 14 hours of darkness. Lights was opened at 06:00, and closed at 16h00.
d) Diet:
During the acclimation period, rats received a commercial rodent diet (Purina, # 5075) and tap water ad libitum. During study period, groups 1 & 2 continued to receive the commercial diet while groups 3 to 10 received a high sucrose-high fat diet composed of (g/100 g): Sucrose, 45; Corn oil, 10; Lard, 10; Casein, 22.5; dl-Methionine, 0.3; Vitamin mix, 1.2; AIN-76 mineral mix, 5.5; Fiber, 5.5.

Rats were fasted (with access to water only) around 22h00 the night prior to their necropsy.

Randomization:
A few days after their arrival, rats were weighed and assigned to each group in order to have groups with equivalent mean body weights.

Methods and Experimental Design

Test Groups
80 rats were assigned to 10 groups of 8 rats for conduct of the study outlined below.

| | | Dose (mg/rat) | |
|---|---|---|---|
| Diet | Treatment | Per os | Topic |
| Chow[1] | INT | 0 | 0 |
| | OVX | 0 | 0 |
| | INT | 0 | 0 |
| | INT + EM-652.HCl | 0.5 | 0 |
| Special Diet[2] | INT + DHEA | 0 | 20 |
| | INT + EM-652.HCl + DHEA | 0.5 | 20 |
| | OVX | 0 | 0 |
| | OVX + EM-652.HCl | 0.5 | 0 |
| | OVX + DHEA | 0 | 20 |
| | OVX + EM-652.HCl + DHEA | 0.5 | 20 |

[1]Commercial rodent chow
[2]High sucrose-high fat diet

Animal Preparation
On day 0 of the study, rats from the appropriate groups were ovariectomized (by bilateral flank incision) under Isoflurane anesthesia. Intact rats were sham-operated.

Dosing
Administration of the tested compounds or vehicle started the day following the ovariectomy (Day 1). The tested compound EM-652.HCl was given as suspension in 0.4% methylcellulose by oral gavage (0.5 ml/gavage/rat) once daily for 20 days while the DHEA was applied topically on dorsal skin (0.5 ml/application/rat) once daily for the same period. Rats from control groups received the vehicle alone (per os and topically). Rats were killed on day 21 of the study approximately 24 hours after the last dosing.

Body Weights
Rats were weighed on day 0 (surgery), every 2 days during the study period and on the day of necropsy. Body weights were recorded with a precision of 1.0 g.

Food Consumption
Food consumption was evaluated every 2 days during the study period.

Method of Sacrifice
On day 21 of the study, overnight fasted rats were killed approximately 24 hours after the last dosing. They were anesthesized with ketamine-xylazine and blood drawn by cardiac punction.

Blood Samples

Blood lipids (Total cholesterol and Triglycerides) were measured on frozen serum samples using the Boehringer Mannheim Diagnostic Hitachi 911 Analyzer (Boehringer Mannheim Diagnostic Laboratory Systems). Circulating hormones and substrates (Insulin, leptin, glucose) were measured on serum samples as follow:

Insulin: Linco RIA kit

Glucose: Beckmann automatic glucose analyser

Leptin: Linco RIA kit

Organs and Tissues Collected

The following tissues were collected and weighed for all animals:

Muscle (soleus and VLM), fat (retroperitoneal and inguinal), and, brown adipose tissue.

A piece of liver was frozen for later determination of TG and CHOL content (Folchis method) while the other tissues were processed for determination of LPL activity.

Results

TABLE 9

| GROUP | | Total weight | White adipose tissue inguinal | | White adipose tissue retroperitoneal | | Brown adipose tissue | |
|---|---|---|---|---|---|---|---|---|
| | | | weight | Lipoprotein lipase activity µU/g | weight | Lipoprotein lipase activity µU/g | weight | Lipoprotein lipase activity µU/g |
| diet | treatment | g | g | protein | g | protein | g | protein |
| chow | sham control | 239 ± 6 | 0.410 ± 0.043 | 252 ± 55 | 0.983 ± 0.104 | 1526 ± 217 | 0.329 ± 0.035 | 1053 ± 138 |
| chow | OVX control | 294 ± 6 | 0.888 ± 0.146 | 570 ± 100 | 1.472 ± 0.199 | 2415 ± 147 | 0.466 ± 0.041 | 688 ± 88 |
| Sucrose + fat | sham control | 257 ± 10 | 0.716 ± 0.107 | 344 ± 73 | 1.765 ± 0.292 | 1470 ± 242 | 0.376 ± 0.033 | 1073 ± 152 |
| Sucrose + fat | Sham + EM-652.HCl | 238 ± 5 | 0.435 ± 0.043 | 160 ± 23 | 1.058 ± 0.162 | 1277 ± 56 | 0.306 ± 0.044 | 1196 ± 83 |
| Sucrose + fat | Sham + DHEA | 252 ± 5 | 0.659 ± 0.075 | 194 ± 45 | 1.067 ± 0.149 | 1177 ± 188 | 0.373 ± 0.036 | 982 ± 72 |
| Sucrose + fat | Sham + EM-652.HCl + DHEA | 249 ± 4 | 0.489 ± 0.083 | 224 ± 45 | 0.909 ± 0.124 | 1349 ± 133 | 0.322 ± 0.026 | 885 ± 78 |
| Sucrose + fat | OVX control | 316 ± 8 | 1.800 ± 0.251 | 725 ± 106 | 3.058 ± 0.297 | 2503 ± 215 | 0.519 ± 0.064 | 867 ± 99 |
| Sucrose + fat | OVX + EM-652.HCl | 268 ± 5 | 0.709 ± 0.085 | 310 ± 63 | 1.370 ± 0.211 | 1612 ± 186 | 0.408 ± 0.025 | 678 ± 65 |
| Sucrose + fat | OVX + DHEA | 274 ± 9 | 0.885 ± 0.156 | 583 ± 134 | 1.699 ± 0.151 | 1905 ± 112 | 0.342 ± 0.049 | 1069 ± 96 |
| Sucrose + fat | OVX + EM-652.HCl + DHEA | 263 ± 5 | 0.658 ± 0.088 | 306 ± 42 | 1.436 ± 0.162 | 1542 ± 118 | 0.373 ± 0.040 | 876 ± 75 |

| Group | | Soleus muscle | | Vastus Lateralis muscle | | liver | |
|---|---|---|---|---|---|---|---|
| | | weight | Lipoprotein lipase activity | weight | Lipoprotein lipase activity | total cholesterol | triglycerides |
| diet | treatment | g | µU/g protein | g | µU/g protein | mmol/L | mmol/L |
| chow | sham control | 0.106 ± 0.002 | 62.7 ± 3.0 | 0.872 ± 0.027 | 11.7 ± 3.5 | 0.076 ± 0.004 | 0.134 ± 0.019 |
| chow | OVX control | 0.116 ± 0.005 | 43.8 ± 3.3 | 1.000 ± 0.042 | 13.1 ± 3.7 | 0.082 ± 0.004 | 0.169 ± 0.027 |
| Sucrose + fat | sham control | 0.096 ± 0.005 | 55.0 ± 5.1 | 0.927 ± 0.040 | 13.1 ± 3.2 | 0.083 ± 0.002 | 0.123 ± 0.014 |
| Sucrose + fat | Sham + EM-652.HCl | 0.098 ± 0.005 | 53.9 ± 3.3 | 0.965 ± 0.034 | 16.2 ± 3.1 | 0.096 ± 0.011 | 0.360 ± 0.102 |
| Sucrose + fat | Sham + DHEA | 0.105 ± 0.004 | 53.6 ± 7.5 | 0.893 ± 0.043 | 11.5 ± 2.0 | 0.068 ± 0.003 | 0.038 ± 0.007 |
| Sucrose + fat | Sham + EM-652.HCl + DHEA | 0.098 ± 0.005 | 56.6 ± 4.5 | 0.971 ± 0.029 | 19.5 ± 3.5 | 0.101 ± 0.008 | 0.184 ± 0.033 |
| Sucrose + fat | OVX control | 0.110 ± 0.004 | 39.2 ± 3.9 | 1.037 ± 0.026 | 10.9 ± 1.82 | 0.097 ± 0.007 | 0.262 ± 0.052 |
| Sucrose + fat | OVX + EM-652.HCl | 0.104 ± 0.004 | 39.1 ± 5.0 | 0.944 ± 0.030 | 10.8 ± 3.2 | 0.092 ± 0.006 | 0.348 ± 0.078 |
| Sucrose + fat | OVX + DHEA | 0.103 ± 0.005 | 45.9 ± 4.7 | 0.920 ± 0.049 | 13.1 ± 5.4 | 0.079 ± 0.005 | 0.165 ± 0.047 |
| Sucrose + fat | OVX + EM-652.HCl + DHEA | 0.101 ± 0.001 | 48.4 ± 4.8 | 0.929 ± 0.038 | 11.0 ± 4.1 | 0.106 ± 0.008 | 0.273 ± 0.031 |

| GROUP | | Plasma insulin | Plasma glucose | Plasma total cholesterol | Plasma triglycerides | Plasma leptin |
|---|---|---|---|---|---|---|
| diet | treatment | nmol/L | mmol/L | mmol/L | mmol/L | ng/mL |

TABLE 9-continued

| | | | | | | |
|---|---|---|---|---|---|---|
| chow | sham control | 0.071 ± 0.010 | 7.56 ± 0.24 | 1.61 ± 0.17 | 0.49 ± 0.12 | 1.404 ± 0.224 |
| chow | OVX control | 0.146 ± 0.027 | 8.69 ± 0.57 | 2.10 ± 0.10 | 0.68 ± 0.10 | 2.388 ± 0.737 |
| Sucrose + fat | sham control | 0.079 ± 0.013 | 9.07 ± 0.48 | 1.60 ± 0.12 | 0.66 ± 0.17 | 3.572 ± 0.699 |
| Sucrose + fat | Sham + EM-652.HCl | 0.057 ± 0.004 | 9.03 ± 0.49 | 1.15 ± 0.06 | 0.60 ± 0.12 | 2.019 ± 0.402 |
| Sucrose + fat | Sham + DHEA | 0.048 ± 0.012 | 8.05 ± 0.51 | 1.59 ± 0.17 | 0.61 ± 0.11 | 1.977 ± 0.255 |
| Sucrose + fat | Sham + EM-652.HCl + DHEA | 0.049 ± 0.013 | 7.99 ± 0.44 | 0.93 ± 0.08 | 0.95 ± 0.21 | 1.071 ± 0.162 |
| Sucrose + fat | OVX control | 0.125 ± 0.022 | 10.46 ± 0.72 | 1.62 ± 0.26 | 0.83 ± 0.13 | 7.900 ± 1.982 |
| Sucrose + fat | OVX + EM-652.HCl | 0.089 ± 0.013 | 9.06 ± 0.30 | 1.15 ± 0.11 | 0.97 ± 0.16 | 1.989 ± 0.326 |
| Sucrose + fat | OVX + DHEA | 0.052 ± 0.009 | 8.64 ± 0.24 | 1.57 ± 0.12 | 0.62 ± 0.08 | 2.757 ± 0.631 |
| Sucrose + fat | OVX + EM-652.HCl + DHEA | 0.060 ± 0.010 | 8.65 ± 0.38 | 0.87 ± 0.09 | 0.92 ± 0.21 | 1.672 ± 0.327 |

Example 10

Effect of EM-652.HCl, ERA-923, Lasofoxifene, LY 353381 and Raloxifene on energy balance and lipid-lipoprotein metabolism in ovariectomized female rats. URMA-r-45-00

The objective of this study was to determine the effect on energy balance and lipid-lipoprotein metabolism in rats following treatment with different selective estrogen receptor modulators described in the literature and to compare the results obtained with those of EM-652.HCl. For this purpose, tested compounds were administered by oral gavage for 20 days (0.5 mg/rat for each compound; 0.5 ml/rat) in 0.4% methylcellulose to ovariectomized female rats. Intact control, ovariectomized (OVX) control and OVX rats treated with 17-estradiol (E2) were used as reference.

Test Animal

Species :*Rattus norvegicus*
Strain: Sprague-Dawley Rat (Crl:CD® (SD) BR VAF/PlusTM)
Sex: Female
Body Weight: At onset of dosing, body weights were approximately 200–225 g .
Housing and maintenance
a) Housing:
The rats were housed individually in stainless steel cages of conventional design during the acclimation and study periods
b) Temperature:
Environmental conditions (temperature, humidity) in the rat room were recorded continuously using a computerized automated system. The targeted conditions were of 22±3 C. and 50±20% relative humidity.
c) Light-Dark Cycle:
The photoperiod was 10 hours of light and 14 hours of darkness. Lights were opened at 07:15, and closed at 17h15.
d) Diet:
During acclimation period, rats received a certified rodent diet (Lab Diet # 5002, pellet) and tap water ad libitum while during study period, they received a high carbohydrate diet (diet # 3) and tap water ad libitum. The diet was composed of (g/100 g): Corn starch, 31.2; Dextrose, 31.2; Casein, 20.0; corn oil, 6.4; dl-Methionine, 0.3; Vitamine mix, 1.0; AIN-76 mineral mix, 4.9; fiber, 5.0. Rats were fasted (with access to water only) around 07h00 the morning of their necropsy Randomization:

Rats were assigned to each group in order to have equivalent mean body weights.

Methods and Experimental Design

Test groups: Seventy-seven rats were assigned to 8 groups of 9–10 rats for conduct of the study outlined below.

| | | Dosing suspensions | |
|---|---|---|---|
| Nb of rat group | Treatment | Dose (mg/kg) | Vol./rat (ml) |
| 9 | Intact | 0 | 0.5 ml |
| 9 | OVX | 0 | 0.5 ml |
| 10 | OVX + EM-652.HCl | 0.5 | 0.5 ml |
| 10 | OVX + ERA-923 (EM-3527) | 0.5 | 0.5 ml |
| 10 | OVX + Lasofoxifene (EM-3555) | 0.5 | 0.5 ml |
| 10 | OVX + LY 353381 (em-1665) | 0.5 | 0.5 ml |
| 10 | OVX + Raloxifene (EM-1105) | 0.5 | 0.5 ml |
| 9 | OVX + E | 0.5 | 0.5 ml |

Animal Preparation

On the 0 of the study, rats from group 2 to 8 were ovariectomized (by bilateral flank incision) under Isoflurane anesthesia. Rats from group 1 were sham-operated.

Body Weights

Rats were weighed on day 0 (surgery) and then, every 2 days during study period as well as on the day of necropsy.

Food Consumption

Food consumption was evaluated every 2 days.

Body Composition (Fat Percentage)

In order to determine the effect of treatments on fat percentage, body composition were measured on Day 17 of the study using dual energy x-ray absorptiometry (DEXA; QDR 4500A, Hologic, Waltham, Mass.).

Method of Sacrifice

On day 21 of the study, approximately 24 hours after the last dosing and 6 hours of fasting, animals under Ketamine-Xylazine anesthesia were killed by exsanguination at the abdominal aorta.

Blood Samples

Blood lipids (Total cholesterol and Triglycerides) and glucose were measured on frozen serum samples using the Boehringer Mannheim Diagnostic Hitachi 911 Analyzer (Boehringer Mannheim Diagnostic Laboratory Systems). Circulating hormones and substrates (Insulin and leptin) were measured on serum sample using the following kits:

Insulin: Linco RIA kit
Leptin: Linco RIA kit

Organs and Tissues Collected

The following tissues were collected and weighed:

Muscle (right soleus and right VLM), fat (right retroperitoneal and right inguinal), and brown adipose tissue.

A piece of ~0.1 g of all tissues (except uterus and vagina) were frozen in liquid nitrogen and kept at −80 C. for later determination of lipoprotein-lipase (LPL) activity.

Results

TABLE 10

| Treatment | Total weight g | White adipose tissue inguinal | | White adipose tissue retroperitoneal | | Brown adipose tissue | |
|---|---|---|---|---|---|---|---|
| | | weight g | Lipoprotein lipase activity µU/g protein | weight g | Lipoprotein lipase activity µU/g protein | weight g | Lipoprotein lipase activity µU/g protein |
| intact | 232 ± 7 | 0.350 ± 0.037 | 379 ± 69 | 1.31 ± 0.09 | 1537 ± 253 | 0.410 ± 0.030 | 973 ± 115 |
| OVX | 284 ± 5 | 0.320 ± 0.048 | 797 ± 97 | 1.55 ± 0.15 | 2664 ± 338 | 0.380 ± 0.027 | 880 ± 130 |
| OVX + EM-652.HCl | 252 ± 4 | 0.244 ± 0.028 | 684 ± 216 | 1.32 ± 0.21 | 1917 ± 365 | 0.339 ± 0.038 | 900 ± 91 |
| OVX + ERA-923 | 260 ± 5 | 0.326 ± 0.042 | 766 ± 173 | 1.27 ± 0.15 | 1750 ± 140 | 0.350 ± 0.019 | 1017 ± 83 |
| OVX + Lasofoxifene | 210 ± 2 | 0.187 ± 0.023 | 801 ± 138 | 0.867 ± 0.132 | 1417 ± 163 | 0.244 ± 0.022 | 982 ± 98 |
| OVX + LY 353381 | 231 ± 4 | 0.290 ± 0.038 | 559 ± 165 | 0.968 ± 0.120 | 1365 ± 119 | 0.368 ± 0.031 | 888 ± 65 |
| OVX + Raloxifene | 230 ± 3 | 0.245 ± 0.047 | 579 ± 46 | 1.32 ± 0.24 | 1510 ± 52 | 0.307 ± 0.26 | 960 ± 116 |
| OVX + $E_2$ | 198 ± 4 | 0.158 ± 0.019 | 416 ± 74 | 0.550 ± 0.102 | 1442 ± 243 | 0.211 ± 0.021 | 1198 ± 62 |

| Treatment | Soleus muscle | | Vastus Lateralis muscle | |
|---|---|---|---|---|
| | weight g | Lipoprotein lipase activity µU/g protein | weight g | Lipoprotein lipase activity µU/g protein |
| Intact | 0.113 ± 0.020 | 17.2 ± 2.2 | 0.924 ± 0.031 | ND |
| OVX | 0.108 ± 0.006 | 17.6 ± 3.9 | 0.963 ± 0.045 | ND |
| OVX + EM-652.HCl | 0.118 ± 0.018 | 14.5 ± 4.1 | 1.00 ± 0.047 | ND |
| OVX + ERA-923 | 0.100 ± 0.004 | 11.7 ± 1.9 | 0.993 ± 0.33 | ND |
| OVX + Lasofoxifene | 0.096 ± 0.003 | 10.9 ± 1.5 | 0.800 ± 0.048 | ND |
| OVX + LY 353381 | 0.092 ± 0.002 | 10.1 ± 1.0 | 0.955 ± 0.20 | ND |
| OVX + Raloxifene | 0.099 ± 0.003 | 10.2 ± 2.0 | 0.795 ± 0.055 | ND |
| OVX + $E_2$ | 0.086 ± 0.003 | 10.9 ± 2.0 | 0.718 ± 0.026 | ND |

| Treatment | Cumulative food intake g | Serum insulin nmol/L | Serum glucose mmol/L | Serum total cholesterol mmol/L | Serum triglycerides mmol/L | Serum leptin ng/mL |
|---|---|---|---|---|---|---|
| Intact | 332 ± 14 | 0.086 ± 0.11 | 13.6 ± 0.6 | 2.41 ± 0.16 | 0.62 ± 0.07 | 2.46 ± 0.37 |
| OVX | 389 ± 8 | 0.178 ± 0.030 | 15.9 ± 1.9 | 2.58 ± 0.11 | 0.63 ± 0.05 | 3.48 ± 0.40 |
| OVX + EM-652.HCl | 324 ± 5 | 0.122 ± 0.021 | 15.9 ± 1.4 | 1.41 ± 0.09 | 0.91 ± 0.17 | 1.10 ± 0.22 |
| OVX + ERA-923 | 347 ± 9 | 0.113 ± 0.029 | 16.5 ± 2.7 | 1.66 ± 0.16 | 0.93 ± 0.24 | 2.12 ± 0.44 |
| OVX + Lasofoxifene | 283 ± 14 | 0.095 ± 0.017 | 15.8 ± 1.3 | 1.29 ± 0.06 | 0.81 ± 0.21 | 0.97 ± 0.29 |
| OVX + LY 353381 | 312 ± 7 | 0.104 ± 0.11 | 17.1 ± 0.7 | 1.15 ± 0.08 | 1.23 ± 0.28 | 1.22 ± 0.21 |
| OVX + Raloxifene | 307 ± 8 | 0.077 ± 0.10 | 13.8 ± 1.2 | 1.19 ± 0.08 | 1.20 ± 0.35 | 1.39 ± 0.30 |
| OVX + $E_2$ | 255 ± 9 | 0.070 ± 0.007 | 11.8 ± 1.4 | 2.03 ± 0.15 | 0.43 ± 0.04 | 0.309 ± 0.097 |

ND = Not Determined

Example 11
Effect of compounds of the invention as well as prior art compounds on alkaline phosphatase activity in human endometrial adenocarcinoma Ishikawa cells.

Materials
Maintenance of Stock Cell Cultures

The human Ishikawa cell line derived from a well differentiated endometrial adenocarcinoma was kindly provided by Dr. Erlio Gurpide, The Mount Sinai Medical Center, New York, N.Y. The Ishikawa cells were routinely maintained in Eagle's Minimum Essential Medium (MEM) containing 5% (vol/vol) FBS and supplemented with 100 U/ml penicillin, 100 µg/ml streptomycin, 0.1 mM Non-essential Amino Acids solution. Cells were plated in Falcon T75 flasks at a density of 1.5×106 cells at 37 C.

Cell Culture Experiments

Twenty four hours before the start of an experiment, the medium of near confluent Ishikawa cells was replaced by fresh estrogen-free basal medium (EFBM) consisting of a 1:1 (v:v) mixture of phenol red-free Ham's F-12 and Dulbecco's Modified Eagle's Medium (DMEM) supplemented with 100 U/mL penicillin, 100 µg/mL Streptomycin, 2 mM glutamine, and 5% FBS treated twice with dextran-coated charcoal to remove endogenous steroids. Cells were then harvested by 0.1% pancreatin (Sigma) and 0.25 mM HEPES, resuspended in EFBM and plated in Falcon 96 well flat-bottomed microtiter plates at a density of 2.2×104 cells/well in a volume of 100 µl and allowed to adhere to the surface of the plates for 24 h. Thereafter, medium was replaced with fresh EFBM containing the indicated concentrations of compounds in a final volume of 200 µl. Cells were incubated for five days, with a medium change after 48 h.

Alkaline Phosphatase Assay

At the end of the incubation period, microtiter plates were inverted and growth medium was decanted. The plates were rinsed with 200 µL by well of PBS (0.15M NaCl, 10 mM sodium phosphate, pH 7.4). PBS was then removed from the plates while carefully leaving some residual PBS, and the wash procedure was repeated once. The buffered saline was then decanted, and the inverted plates were blotted gently on a paper towel. Following replacement of the covers, the plates were placed at −80 C. for 15 min followed by thawing at room temperature for 10 min. The plates were then placed on ice, and 50 µl of an ice-cold solution containing 5 mM p-nitrophenyl phosphate, 0.24 mM MgCl2, and 1 M diethanolamine (pH 9.8) was added. Plates were then warmed to room temperature, and the yellow color from the production of p-nitrophenyl was allowed to develop (8 min). Plates were monitored at 405 nm in an enzyme-linked immunosorbent assay plate reader (BIO-RAD, model 2550 EIA Reader).

Calculations

Dose-response curves as well as IC50 values were calculated using a weighted iterative nonlinear squares regression.

TABLE 11

| NAME | CODE NAME | STRUCTURE | Stimulation of alkaline phosphatase by tested compounds % of 1 nM $E_2$ stimulation* (nb of experiments) | Inhibition of 1 nM $E_2$ stimulation of alkaline phosphatase by tested compounds $IC_{50}$ (nM) (nb of experiments) |
|---|---|---|---|---|
| EM-652.HCl | EM-652.HCl; EM-1538 | 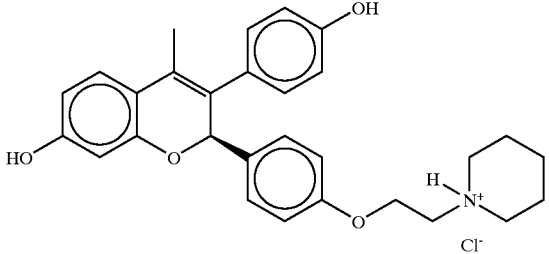 | 1.88 ± 0.26 (22) | 1.52 ± 0.22 (18) |
| OH-Tamoxifen | EM-882 | 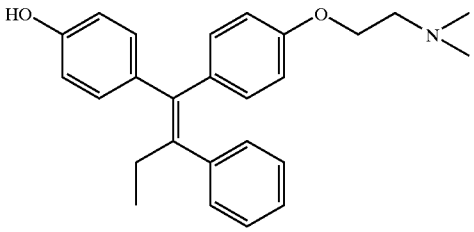 | 32.4 ± 2.2 (8) | 31.9 ± 6.0 (5) |
| OH-Toremifene | EM-880 | 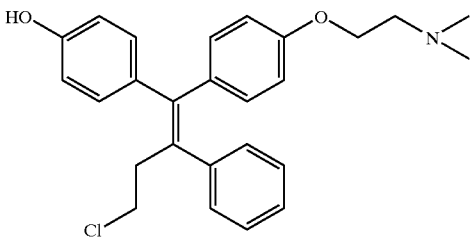 | 29.6 ± 2.1 (6) | 72.1 ± 7.6 (3) |
| Idoxifene | EM-1750 | 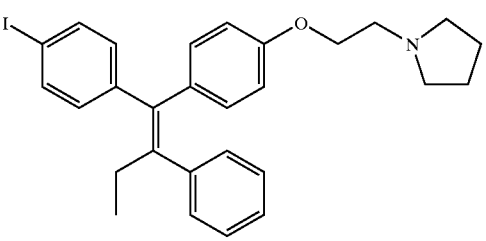 | 25.1 ± 1.5 (5) | >1000 (2) |
| GW-5638 | EM-1796 | 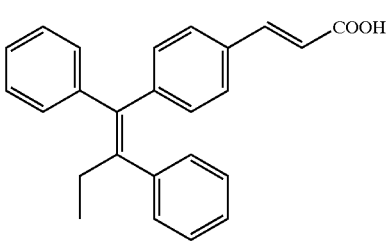 | 7.75 ± 5.5 (2) | No inhibition |

TABLE 11-continued

| NAME | CODE NAME | STRUCTURE | Stimulation of alkaline phosphatase by tested compounds % of 1 nM $E_2$ stimulation* (nb of experiments) | Inhibition of 1 nM $E_2$ stimulation of alkaline phosphatase by tested compounds $IC_{50}$ (nM) (nb of experiments) |
|---|---|---|---|---|
| Droloxifene | EM-835 | 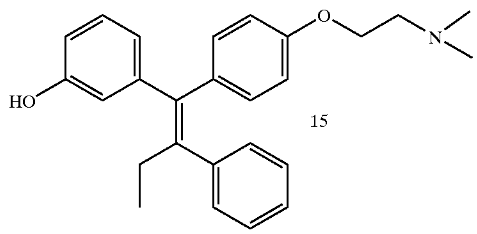 | 23.8 ± 3.1 (7) | 291 ± 115 (4) |
| Raloxifene LY 156758 | EM-1105 | 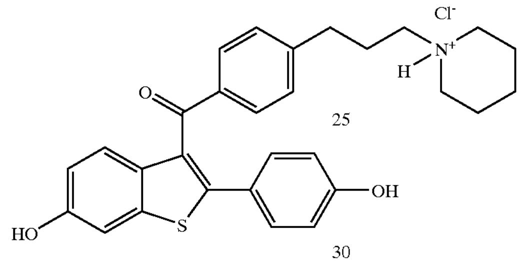 | 12.8 ± 1.7 (8) | 3.39 ± 0.9 (6) |
| LY 353381 | EM-1665 | 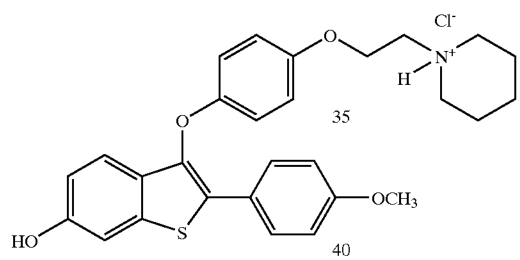 | 15.5 ± 0.25 (5) | 1.87 ± 0.07 (2) |
| Lasofoxifene (free base) | EM-3114 | 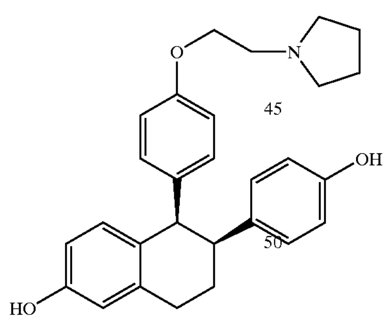 | 17.9 (1) | 4.24 (1) |
| ERA-923 | EM-3527 | 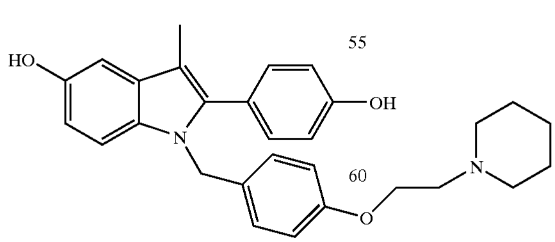 | 0.6 (1) | 5.84 (1) |

*% of 1 nM $E_2$ stimulation = OD 405 nm compound-OD 405 nm basal/OD 405 nm 1 nM $E_2$-OD 405 nm basal Please see also Labrie et al. EM-652 (SCH 57068), a third generation SERM[65] acting as pure antiestrogen in the mammary gland and endometrium, J. Steroid Biochem. and Mol. Bio. 69, 51–84, 1999.

Example 12
Effect of EM-652.HCl and FCE 424 on the proliferation of human breast cancer MCF-7 cell line Methods Maintenance of Stock Cell Cultures MCF-7 human breast cancer cells were obtained from the American Type Culture Collection # HTB 22 at passage 147 and routinely grown in phenol red-free Dulbecco's Modified Eagle's-Ham's F12 medium, the supplements mentioned above and 5% FBS. The MCF-7 human breast adenocarcinoma cell line was derived from the pleural effusion of a Caucasian 69-year-old female patient. MCF-7 cells were used between passages 148 and 165 and subcultured weekly.

Cell Proliferation Studies

Cells in their late logarithmic growth phase were harvested with 0.1% pancreatin (Sigma) and resuspended in the appropriate medium containing 50 ng bovine insulin/ml and 5% (v/v) FBS treated twice with dextran-coated charcoal to remove endogenous steroids. Cells were plated in 24-well Falcon plastic culture plates (2 cm2/well) at the indicated density and allowed to adhere to the surface of the plates for 72 h. Thereafter, medium was replaced with fresh medium containing the indicated concentrations of compounds diluted from 1000×stock solutions in 99% redistilled ethanol in the presence or absence of E2. Control cells received only the ethanolic vehicle (0.1% EtOH,v/v). Cells were incubated for the specified time intervals with medium changes at 2-or 3-day intervals. Cell number was determined by measurement of DNA content.

Calculations and Statistical Analysis

Dose-response curves as well IC50 values were calculated using a weighted iterative nonlinear least-squares regression. All results are expressed as means±SEM.

TABLE 12

| NAME | CODE NAME | Stimulation of DNA by tested compounds % of 1 nM E2 stimulation * | Inhibition of 1 nM E2 stimulation of DNA by tested compounds IC50 (nM) |
|---|---|---|---|
| EM-652.HCl | EM-652.HCl; EM-1538 | N.S. | 0.796 |
| ERA-923 | EM-3527 | N.S. | 3.68 |

Example 13
Comparative effect on uterine weight, fat, and lipid of EM-652.HCl. TSE 424 and lasofoxifene, administered alone or in combination with EM-6562.HCl, to ovariectomized female rats.
URMA-r-44-00

The objective of this study was to compare the effect on uterine, weight, fat and blood lipids following treatment with EM-652.HCl, ERA-923 and lasofoxifene, administered alone or in combination with EM-652.HCl, to ovariectomized female rats. For this purpose, each compound was administered orally for 20 days to ovariectomized female rats and at the end of the treatment period, the uterus and fat were collected and weighed.

Test Animal Specifications
  Species: *Rattus norvegicus*
  Strain: Sprague-Dawley Rat (Crl:CD® (SD) BR VAF/PlusTM)
  Sex: Female
  Body Weight: At onset of dosing, body weights were approximately 225–250 g.

Housing and maintenance
  a) Housing:
    The rats were housed individually in stainless steel cages of conventional design during the acclimation and study periods.
  b) Temperature and Humidity:
    Environmental conditions (temperature, humidity) in the rat room were recorded continuously using a computerized automated system. The targeted conditions was of 22±3 C. and 50±20% relative humidity.
  c) Light-Dark Cycle:
    The photoperiod was 12 hours of light and 12 hours of darkness. These parameters were recorded continuously using a validated computerized automated system. Lights were on from 07:15 to 19:15.
  d) Diet:
    Certified Rodent feed (Lab Diet # 5002, pellets) and tap water were provided ad libitum.

Randomization:

Rats were assigned to each group at random at the time of ovariectomy.

Test Groups

Seventy rats were separated into 7 groups of 9 to 11 animals for conduct of the study outlined below:

| TREATMENT | DOSING SUSPENSIONS |
|---|---|
| INTACT | — |
| OVX | — |
| OVX + EM-652.HCl | 0.5 |
| OVX + EM-3527 | 0.5 |
| OVX + EM-652.HCl + EM-3527 | 2.5 + 0.5 |
| OVX-EM-3555 | 0.5 |
| OVX + EM-652.HCl + EM-3555 | 2.5 + 0.5 |

Animal Preparation

Animals from groups 2 to 7 were ovariectomized under Isoflurane-induced anesthesia on Day 1 of the study.

Dosing

The vehicle or tested compounds were given as suspension in 0.4% methylcellulose by oral gavage (0.5 ml/gavage/rat) from Day 2 to Day 21 of the study.

Body Weights

Rats were weighed on Study Day 1 and at the necropsy (SD 22).

Method of Sacrifice

Approximately 24 hours after the last dosing, overnight fasted rats under Isoflurane-induced anesthesia were killed by exsanguination at the abdominal aorta.

Orizans and Tissues Collected

Uteri and retroperitonal adipose tissue were removed and weighed.

TABLE 13

| Treatment | Final Body Weight (g) | Retroperitoneal Adipose Tissue (mg) | Uterine Weight (mg) | Cholesterol (mmol/L) |
|---|---|---|---|---|
| Intact | 222 ± 5** | 1.04 ± 0.13* | 485.8 ± 28.4** | 1.52 ± 0.09** |
| OVX | 266 ± 5 | 1.42 ± 0.24 | 152.9 ± 4.7 | 1.91 ± 0.09 |
| OVX + EM-652.HCl | 238 ± 4** | 0.63 ± 0.08** | 173.0 ± 7.1 | 1.00 ± 0.11** |
| OVX + ERA-923 | 248 ± 5** | 0.84 ± 0.09** | 162.6 ± 5.2 | 1.20 ± 0.10** |
| OVX + ERA-923 + EM-652.HCl (2.5 mg) | 241 ± 1** | 0.91 ± 0.17** | 180.2 ± 5.2 | 0.99 ± 0.07** |
| OVX + Lasofoxifene | 210 ± 3** | 0.52 ± 0.05** | 247.4 ± 9.1** | 0.95 ± 0.09** |
| OVX + Lasofoxifene + EM-652.HCl (2.5 mg) | 234 ± 3** | 0.74 ± 0.10** | 182.3 ± 4.6 | 0.95 ± 0.07** |

*, $p < 0.05$;
**, $p < 0.001$,
experimental versus OVX control group

Pharmaceutical Composition Examples

Set forth below, by way of example and not of limitation, are several pharmaceutical compositions utilizing preferred active SERM EM-800 or EM-652.HCl alone or in combination with one of the preferred active a sex steroid precursors DHEA, androst-5-ene-3b,17b-diol 3-acetate or androst-5-ene-3b,17b-diol dihemisuccinate. Other compounds of the invention or combination thereof, may be used in place of (or in addition to) EM-800 or EM-652.HCl, DHEA, androst-5-ene-3b,17b-diol 3-acetate or androst-5-ene-3b,17b-diol dihemisuccinate. The concentration of active ingredient may be varied over a wide range as discussed herein. The amounts and types of other ingredients that may be included are well known in the art. cl Example A The preferred SERMs of the invention are orally administered Tablet

| Ingredient | Weight % (by weight of total composition) |
|---|---|
| EM-652.HCl | 5 |
| Gelatin | 5 |
| Lactose | 73.5 |
| Starch | 16.5 |

Example B

Capsules

| Ingredient | Weight % (by weight of total composition) |
|---|---|
| EM-652.HCl | 5 |
| Lactose hydrous | 80 |
| Starch | 4.8 |
| Cellulose microcrystalline | 9.8 |
| Magnesium stearate | 0.4 |

Pharmaceutical Composition for Combination Therapies

Example C

Tablet

| Ingredient | Weight % (by weight of total composition) |
|---|---|
| EM-652.HCl | 5 |
| DHEA | 15 |
| Gelatin | 5 |
| Lactose | 58.5 |
| Starch | 16.5 |

Example D

Gelatin capsule

| Ingredient | Weight % (by weight of total composition) |
|---|---|
| EM-652.HCl | 5 |
| DHEA | 15 |
| Lactose hydrous | 65 |
| Starch | 4.8 |
| Cellulose microcrystalline | 9.8 |
| Magnesium stearate | 0.4 |

Kit Examples

Set forth below, by way of example and not of limitation, are several kits utilizing preferred active SERM EM-800 or EM-652.HCl and preferred sex steroid precursor DHEA, androst-5-ene-3b,17b-diol 3-acetate or androst-5-ene-3b,17b-diol dihemisuccinate.

Other compounds of the invention or combination thereof, may be used in place of (or in addition to) EM-800 or EM-652.HCl, DHEA, androst-5-ene-3b,17b-diol 3-acetate or androst-5-ene-3b,17b-diol dihemisuccinate. The concentration of active ingredient(s) may be varied over a wide range as discussed herein. The amounts and types of other ingredients that may be included are well known in the art.

Example A
The SERM is orally administered while the sex steroid precursor is percutaneously administered

SERM composition for oral administration (capsules)

| Ingredient | Weight % (by weight of total composition) |
| --- | --- |
| EM-652.HCl | 5 |
| Lactose hydrous | 80 |
| Starch | 4.8 |
| Cellulose microcrystalline | 9.8 |
| Magnesium stearate | 0.4 |

Sex steroid precursor composition for topical administration (gel)

| Ingredient | Weight % (by weight of total composition) |
| --- | --- |
| DHEA | 10 |
| Caprylic-capric Triglyceride (Neobee M-5) | 5 |
| Hexylene Glycol | 15 |
| Transcutol (diehtyleneglycol mono-methyl ether) | 5 |
| Benzyl alcohol | 2 |
| Cyclomethicone (Dow Corning 345) | 5 |
| Ethanol (absolute) | 56 |
| Hydroxypropylcellulose (1500 cps) (KLUCEL) | 2 |

Example B
The SERM and the sex steroid precursor are orally administered
Non-Steroidal Antiestrogen composition for oral administration (capsules)

| Ingredient | Weight % (by weight of total composition) |
| --- | --- |
| EM-652.HCl | 5 |
| Lactose hydrous | 80 |
| Starch | 4.8 |
| Cellulose microcrystalline | 9.8 |
| Magnesium stearate | 0.4 |

Sex steroid precursor composition for oral administration (gelatin capsule)

| Ingredient | Weight % (by weight of total composition) |
| --- | --- |
| DHEA | 15 |
| Cellulose microcrystalline | 84.6 |
| Magnesium stearate | 0.4 |

Other SERMs may be substituted for EM-800 or EM-652.HCl in the above formulations, as well as other sex steroid inhibitors may be substituted for DHEA, androst-5-ene-3b,17b-diol 3-acetate or androst-5-ene-3b,17b-diol dihemisuccinate. More than one SERM or more than one precursor may be included in which case the combined weight percentage is preferably that of the weight percentage for the single precursor or single SERM given in the examples above.

The invention has been described in terms of preferred embodiments and examples, but is not limited thereby. Those of skill in the art will readily recognize the broader applicability and scope of the invention which is limited only by the patent claims herein.

What is claimed is:

1. A method of treating, or reducing the development of obesity comprising administering to a subject in need of such treatment or reduction a therapeutically effective amount of a compound or pharmaceutically acceptable salt thereof of the following formula:

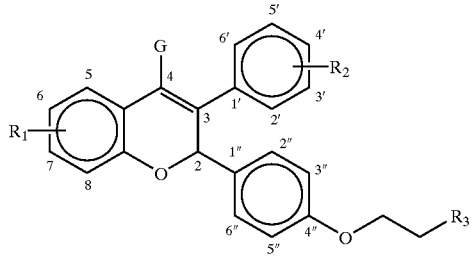

wherein R1 and R2 are independently selected from the group consisting of hydrogen, hydroxyl, —OM (M being selected from the group consisting of straight or branched C1–C4 alkyl, straight or branched C3–C4 alkenyl, straight or branched C3–C4 alkynyl) and a moiety convertible in vivo to hydroxyl;

wherein G is —H or —CH3; and wherein R3 is piperidino.

2. The method of claim 1, wherein the said compound is optically active because it has greater than 50% of a stereoisomer compound having an absolute configuration S on carbon 2.

3. The method of claim 2 wherein said compound or salt substantially lacks (2R)-enantiomer.

4. The method of claim 3 comprising administering to a patient in need of such treatment or reduction a therapeutically effective amount of the following compound:

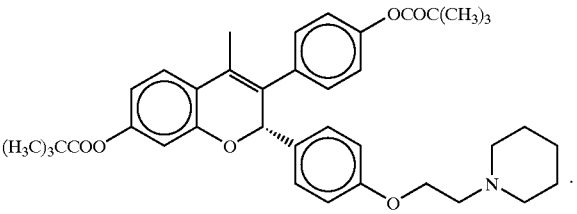

5. The method of claim 1 wherein said compound is a salt of an acid selected from the group consisting of acetic acid, adipic acid, benzenesulfonic acid, benzoic acid, camphorsulfonic acid, citric acid, fumaric acid, hydroiodic acid, hydrobromic acid, hydrochloric acid, hydrochlorothiazide acid, hydroxy-naphthoic acid, lactic acid, maleic acid, methanesulfonic acid, methylsulfuric acid, 1,5-naphthalenedisulfonic acid, nitric acid, palmitic acid, pivalic acid, phosphoric acid, propionic acid, succinic acid, sulfuric acid, tartaric acid, terephthalic acid, p-toluenesulfonic acid, and valeric acid.

6. The method of claim 1 wherein the acid is hydrochloric acid.

7. The method of claim 3 comprising administering to a patient in need of such treatment or reduction a therapeutically effective amount of a hydrochloric salt compound of the following structure:

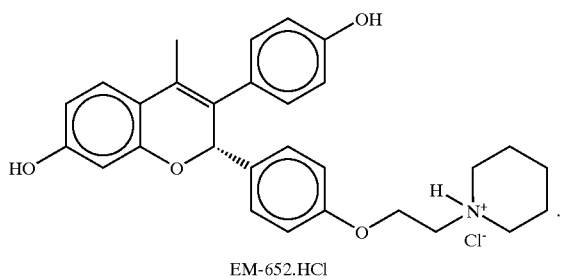

EM-652.HCl

8. A method of treating, or reducing the development of obesity comprising administering to a patient in need of such treatment or reduction of development a therapeutically effective amount of a selective estrogen receptor modulator, and a therapeutically effective amount of estrogen or a steroid selected from the group consisting of dehydroepiandrosterone, dehydroepiandrosterone sulfate, androst-5-ene-3b,17b-diol, and compounds converted in vivo to any of said steroids, wherein the selective estrogen receptor modulator has the following formula:

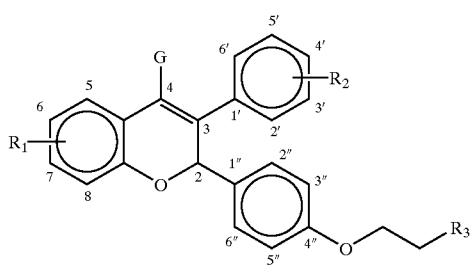

wherein R1 and R2 are independently selected from the group consisting of hydrogen, hydroxyl, —OM (M being selected from the group consisting of straight or branched C1–C4 alkyl, straight or branched C3–C4 alkenyl, straight or branched C3–C4 alkynyl) and a moiety convertible in vivo to hydroxyl;

wherein G is —H or —CH3; and wherein R3 is piperidino.

9. A pharmaceutical composition comprising a pharmaceutically acceptable diluent or carrier, a therapeutically acceptable amount of a selective estrogen receptor modulator having the following formula:

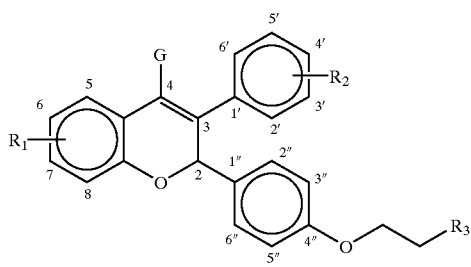

wherein R1 and R2 are independently selected from the group consisting of hydrogen, hydroxyl, —OM (M being selected from the group consisting of straight or branched C1–C4 alkyl, straight or branched C3–C4 alkenyl, straight or branched C3–C4 alkynyl) and a moiety convertible in vivo to hydroxyl;

wherein G is —H or —CH3;

wherein R3 is piperidino; and an estrogen or a sex steroid precursor is selected from the group consisting of dehydroepiandrosterone, dehydroepiandrosterone sulfate, androst-5-ene-3b,17b-diol and compounds converted in vivo to any of said precursors.

10. A pharmaceutical composition comprising a pharmaceutically acceptable excipient diluent or carrier, a therapeutically acceptable amount of a selective estrogen receptor modulator selected from the group consisting of:

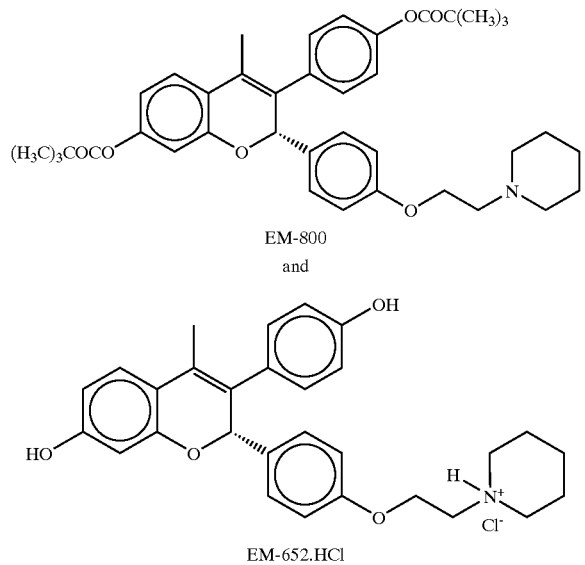

EM-800 and

EM-652.HCl and an estrogen or a sex steroid precursor selected from the group consisting of dehydroepiandrosterone, dehydroepiandrosterone sulfate, androst-5-ene-3b,17b-diol and compounds converted in vivo to either.

11. A method of reducing abdominal fat or reducing the accumulation of abdominal fat comprising administering to a subject in need of such treatment or reduction a therapeutically effective amount of a selective estrogen receptor modulator or pharmaceutically acceptable salt thereof, wherein said selective estrogen receptor modulator has the following formula:

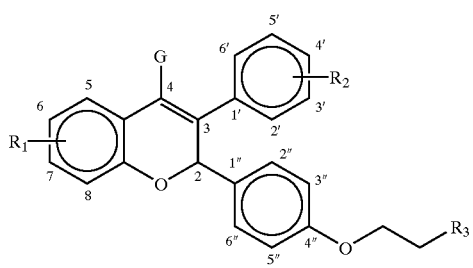

wherein R1 and R2 are independently selected from the group consisting of hydrogen, hydroxyl, —OM (M being selected from the group consisting of straight or branched C1–C4 alkyl, straight or branched C3–C4 alkenyl, straight or branched C3–C4 alkynyl) and a moiety convertible in vivo to hydroxyl;

wherein G is —H or —CH3; and wherein R3 is piperidino.

12. The method of claim 11, wherein said selective estrogen receptor modulator is optically active with greater than 50% of a stereoisomer compound having an absolute configuration S on carbon 2.

13. The method of claim 11 wherein said selective estrogen receptor modulator compound or salt substantially lacks (2R)-enantiomer.

14. The method of claim 12 comprising administering to a patient in need of such treatment or reduction a therapeutically effective amount of the following compound:

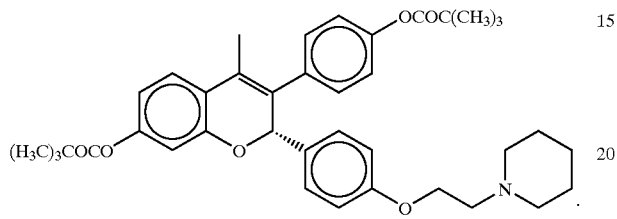

15. The method of claim 11 wherein said compound is a salt of an acid selected from the group consisting of acetic acid, adipic acid, benzenesulfonic acid, benzoic acid, camphorsulfonic acid, citric acid, fumaric acid, hydroiodic acid, hydrobromic acid, hydrochloric acid, hydrochlorothiazide acid, hydroxy-naphthoic acid, lactic acid, maleic acid, methanesulfonic acid, methylsulfuric acid, 1,5-naphthalenedisulfonic acid, nitric acid, palmitic acid, pivalic acid, phosphoric acid, propionic acid, succinic acid, sulfuric acid, tartaric acid, terephthalic acid, p-toluenesulfonic acid, and valeric acid.

16. The method of claim 15 wherein the acid is hydrochloric acid.

17. The method of claim 13 comprising administering to a patient a therapeutically effective amount of a hydrochloric salt compound of the following structure:

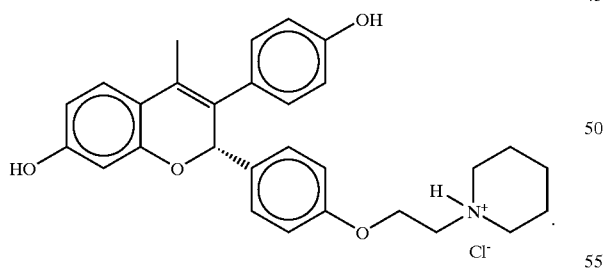

18. A method of reducing abdominal fat or reducing the development of the accumulation of abdominal fat comprising administering to a patient in need of such treatment or reduction a therapeutically effective amount of any selective estrogen receptor modulator, and estrogen or a therapeutically effective amount of a steroid selected from the group consisting of dehydroepiandrosterone, dehydroepiandrosterone sulfate, and androst-5-ene-3b,17b-diol and compounds converted in vivo to any of said precursors, wherein the selective estrogen receptor modulator has the following formula:

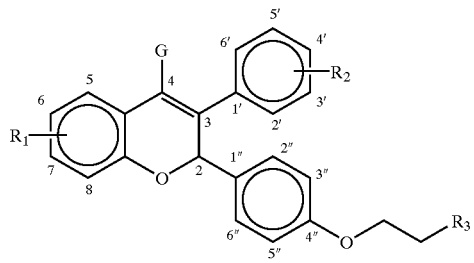

wherein R1 and R2 are independently selected from the group consisting of hydrogen, hydroxyl, —OM (M being selected from the group consisting of straight or branched C1–C4 alkyl, straight or branched C3–C4 alkenyl, straight or branched C3–C4 alkynyl) and a moiety convertible in vivo to hydroxyl;

wherein G is —H or —CH3; and wherein R3 is piperidino.

19. The method of claim 3, wherein said selective estrogen receptor modulator is selected from the group consisting of:

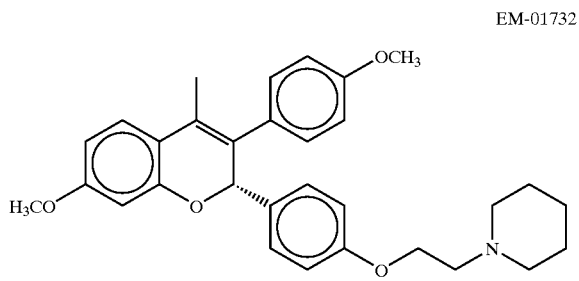

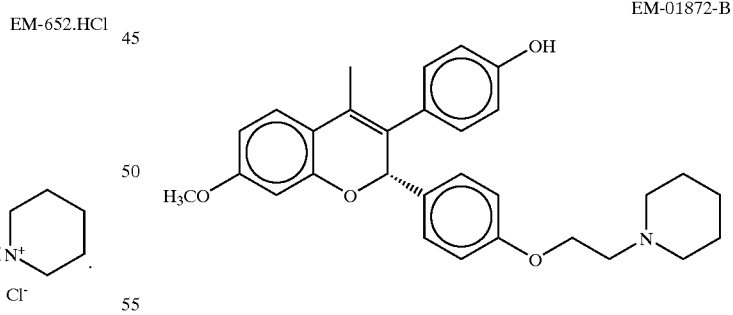

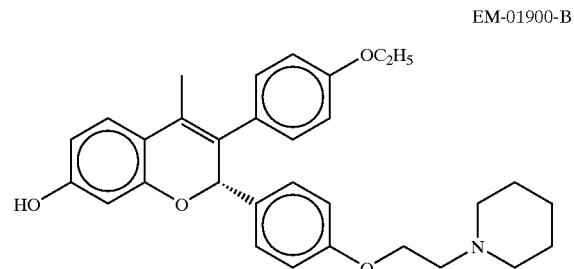

-continued

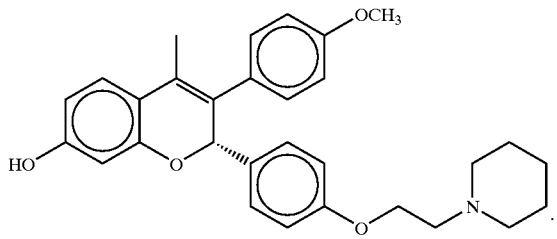
EM-01903-C

20. The method of claim 13, wherein said selective estrogen receptor modulator is selected from the group consisting of:

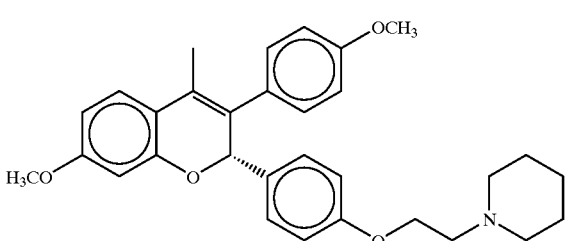
EM-01732

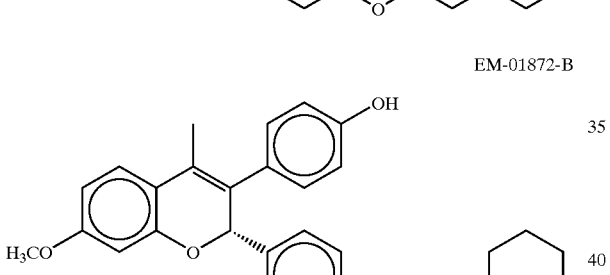
EM-01872-B

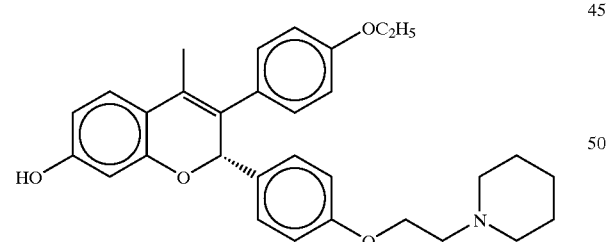
EM-01900-B

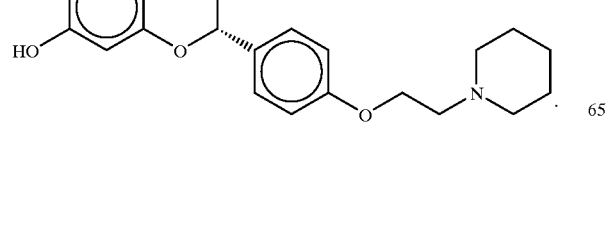
EM-01903-C

21. A pharmaceutical composition comprising a pharmaceutically acceptable excipient diluent or carrier and a therapeutically effective acceptable amount of a selective estrogen receptor modulator selected from the group consisting of:

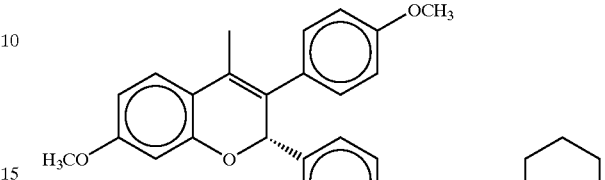
EM-01732

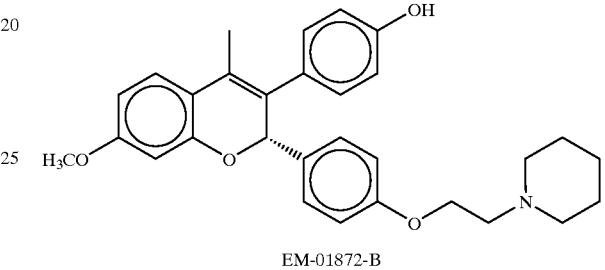
EM-01872-B

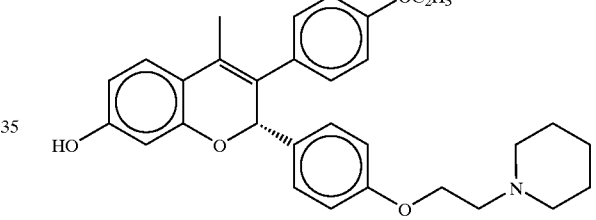
EM-01900-B

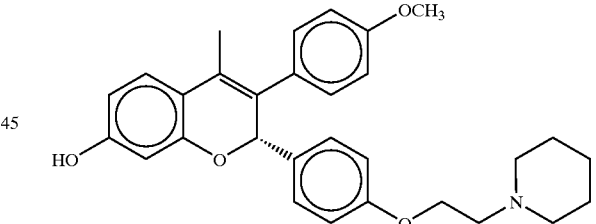
EM-01903-C and an estrogen selected from the group consisting of estradiol and premarin or a sex steroid precursor selected from the group consisting of dehydroepiandrosterone, dehydroepiandrosterone sulfate, androst-5-ene-3b,17b-diol and compounds converted in vivo to either.

22. A method of treating or reducing risk of development of insulin resistance comprising administering to a subject in need of such treatment or reduction a therapeutically effective amount of a selective estrogen receptor modulator, wherein the selective estrogen receptor modulator has the following general formula:

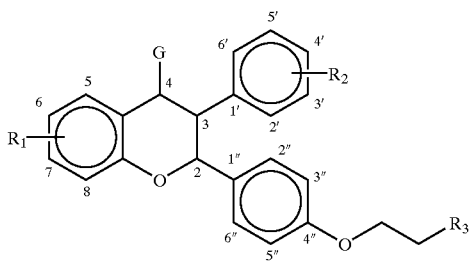

wherein R1 and R2 are independently selected from the group consisting of hydrogen, hydroxyl, —OM (M being selected from the group consisting of straight or branched C1–C4 alkyl, straight or branched C3–C4 alkenyl, straight or branched C3–C4 alkynyl) and a moiety convertible in vivo to hydroxyl;

wherein G is —H or —CH3; and wherein R3 is piperidino.

23. The method of claim 22, further comprising administering a therapeutically effective amount of an estrogen selected from the group consisting of estradiol and premarin or a sex steroid precursor selected from the group consisting of dehydroepiandrosterone, dehydro-epiandrosterone sulfate, androst-5-ene-3b,17b-diol and compounds converted in vivo to either.

24. The method of claim 22, wherein the selective estrogen receptor is

EM-652.HCl

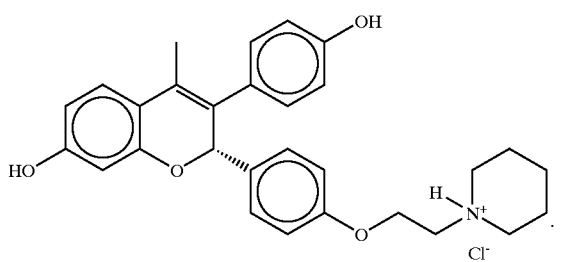

25. A method of reducing blood triglyceride level in a patient in need of such reduction a therapeutically effective amount of a compound or pharmaceutically acceptable salt thereof of the following formula:

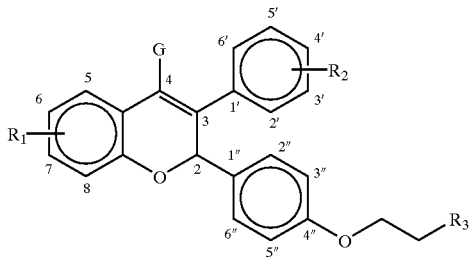

wherein R1 and R2 are independently selected from the group consisting of hydrogen, hydroxyl, —OM (M being selected from the group consisting of straight or branched C1–C4 alkyl, straight or branched C3–C4 alkenyl, straight or branched C3–C4 alkynyl) and a moiety convertible in vivo to hydroxyl;

wherein G is —H or —CH3; and wherein R3 is piperidino.

26. The method of claim 25, wherein the said compound is optically active because it has greater than 50% of a stereoisomer compound having an absolute configuration S on carbon 2.

27. The method of claim 26 wherein said compound or salt substantially lacks (2R)-enantiomer.

28. The method of claim 27 comprising administering to a patient in need of such treatment or reduction a therapeutically effective amount of the following compound:

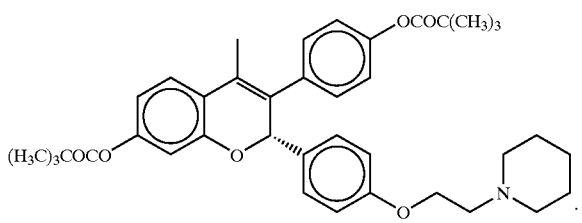

29. The method of claim 25 wherein said compound is a salt of an acid selected from the group consisting of acetic acid, adipic acid, benzenesulfonic acid, benzoic acid, camphorsulfonic acid, citric acid, fumaric acid, hydroiodic acid, hydrobromic acid, hydrochloric acid, hydrochlorothiazide acid, hydroxy-naphthoic acid, lactic acid, maleic acid, methanesulfonic acid, methylsulfuric acid, 1,5-naphthalenedisulfonic acid, nitric acid, palmitic acid, pivalic acid, phosphoric acid, propionic acid, succinic acid, sulfuric acid, tartaric acid, terephthalic acid, p-toluenesulfonic acid, and valeric acid.

30. The method of claim 25 wherein the acid is hydrochloric acid.

31. The method of claim 27 comprising administering to a patient in need of such treatment or reduction a therapeutically effective amount of a hydrochloric salt compound of the following structure:

EM-652.HCl

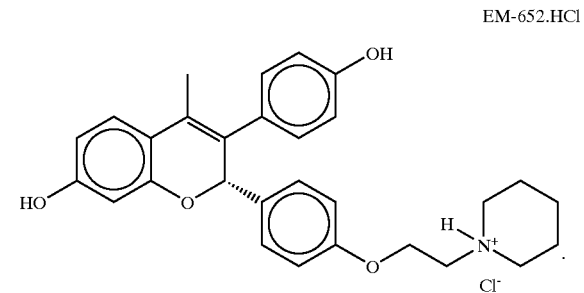

32. A compound of the following molecular structure:
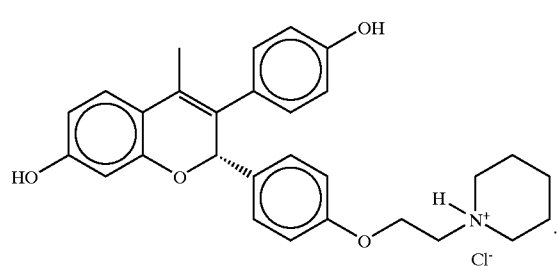
EM-652.HCl
33. A pharmaceutical composition comprising a pharmaceutical excipient, diluent or carrier and a therapeutically effective amount of EM-652.HCl
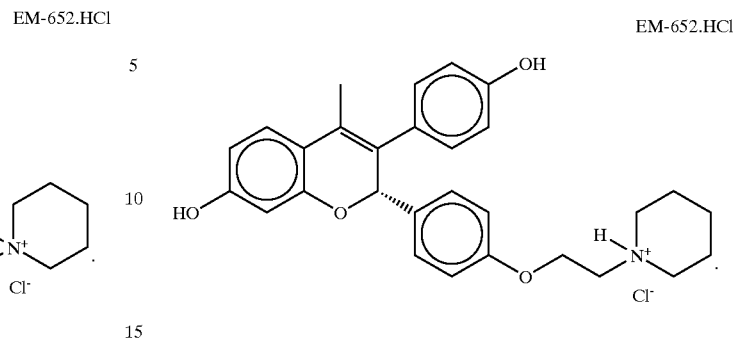
EM-652.HCl
* * * * *